(12) United States Patent
Zumeris et al.

(10) Patent No.: US 7,393,501 B2
(45) Date of Patent: Jul. 1, 2008

(54) METHOD, APPARATUS AND SYSTEM FOR TREATING BIOFILMS ASSOCIATED WITH CATHETERS

(75) Inventors: Jona Zumeris, Nesher (IL); Jacob Levy, Haifa (IL); Yanina Zumeris, Nesher (IL)

(73) Assignee: Nano Vibronix Inc, Cedarhurst, NY (US)

( * ) Notice: Subject to any disclaimer, the term of this patent is extended or adjusted under 35 U.S.C. 154(b) by 205 days.

(21) Appl. No.: 10/445,956

(22) Filed: May 28, 2003

(65) Prior Publication Data
US 2005/0038376 A1 Feb. 17, 2005

Related U.S. Application Data

(60) Provisional application No. 60/383,592, filed on May 29, 2002.

(51) Int. Cl.
*A61L 2/08* (2006.01)
(52) U.S. Cl. .................... 422/20; 422/128; 600/466; 600/467; 604/22; 604/266
(58) Field of Classification Search ............ 422/128, 422/20; 600/466, 467; 604/22, 266
See application file for complete search history.

(56) References Cited

U.S. PATENT DOCUMENTS

| 3,708,263 | A |   | 1/1973 | Boucher |
| 4,216,766 | A | * | 8/1980 | Duykers et al. ............ 600/586 |
| 4,698,058 | A | * | 10/1987 | Greenfeld et al. ........... 604/266 |
| 5,217,018 | A | * | 6/1993 | Dias ........................... 600/463 |
| 5,240,675 | A |   | 8/1993 | Wilk et al. |
| 5,271,735 | A | * | 12/1993 | Greenfeld et al. ............ 604/266 |
| 5,284,148 | A | * | 2/1994 | Dias et al. .................... 600/463 |
| 5,509,417 | A | * | 4/1996 | Dias et al. .................... 600/459 |
| 5,725,494 | A |   | 3/1998 | Brisken |
| 5,728,064 | A | * | 3/1998 | Burns et al. ............ 604/100.01 |
| 5,904,659 | A |   | 5/1999 | Duarte et al. |
| 6,283,921 | B1 |   | 9/2001 | Nix et al. |
| 6,681,783 | B2 | * | 1/2004 | Kawazoe ................. 134/169 C |
| 2002/0065512 | A1 | * | 5/2002 | Fjield et al. ................... 606/27 |
| 2005/0148911 | A1 |   | 7/2005 | Talish et al. |

OTHER PUBLICATIONS

PCT Search Report dated: Sep. 27, 2004 PCT/IL03/00452.
Andrea M. Rediske et al, "Pulsed Ultrasound Enhances the Killing of *Escherichia coli* Biofilms by Aminoglycoside Antibiotics in Vivo", Antimcrobial Agents and Chemotherapy, vol. 44, No. 3, Mar. 2000, pp. 771-772.

(Continued)

*Primary Examiner*—Jill Warden
(74) *Attorney, Agent, or Firm*—Pearl Cohen Zedek Latzer LLP

(57) ABSTRACT

An apparatus, system and method for preventing or treating biofilm associated with catheters. A piezo-ceramic element may be attached to a catheter, and a vibration processor may be connected to the piezo-ceramic element. The vibration processor may provide electric signals that generate acoustic vibrations in the piezo-ceramic element, causing vibrations in or around the catheter. These vibrations may be particularly administered to disperse microbe colonies, thereby preventing or inhibiting formation of biofilm that may lead to infections. Vibrations may be amplified significantly due to resonance conditions in the catheter balloon, which may be powerful enough to be used to disperse microbe colonies that have grouped around the catheter or are attempting to do so.

17 Claims, 16 Drawing Sheets

OTHER PUBLICATIONS

J.M. Schierholz et al., "Implant infections: a haven for opportunistic bacteria", Journal of Hospital Infection, vol. 49, pp. 87-93 (Oct. 2001).

P. Thibon et al., "Randomized multi-centre trial of the effects of a catheter coated with hydrogel and silver salts on the incidence of hospital-acquired urinary tract infections" Journal of Hospital Infection, vol. 45, pp. 117-124, Jun. 2000.

Wendy E. Thomas et al., "Bacterial Adhesion to Target Cells Enhanced by Shear Force", Cell, vol. 109, pp. 913-923, Jun. 28, 2002.

Marvin Whiteley et al., "Identification of genes controlled by quorum sensing in *Pseudomonas aeruginosa*", PNAS, Nov. 23, 1999, vol. 96, No. 24, pp. 13904-13909.

Alvin J. Yamamoto et al., "Sutureless Securement Device Reduces Complications of Peripherally Inserted Central Venous Catheters", J Vasc Interv Radiol., vol. 13, No. 1, 2002, pp. 77-81.

William G. Pitt et al., "Ultrasonic Enhancement of Antibiotic Action on Gram-Negative Bacteria", Antimicrobial Agents and Chemotherapy, vol. 30, No. 11, Nov. 1994, pp. 2577-2582.

Zhen Qian et al., "Investigation of the mechanism of the bioacoustic effect", J. Biomed Mater Res, vol. 44, pp. 198-205, 1999.

John C. Carmen et al., Treatment of Biofilm Infections on Implants with Low-frequency Ultrasound and Antibiotics, Am J Infect Control., Mar. 2005; vol. 33, No. 2, pp. 78-82.

AG Gristina, "Biomaterial-centered infection: microbial adhesion versus tissue integration", Science, vol. 237, Issue 4822, pp. 1588-1595 (Sep. 25, 1987).

Kim Lewis, "Riddle of Biofilm Resistance", Antimicrobial Agents and Chemotherapy, vol. 45, No. 4, Apr. 2001, pp. 999-1007.

E Mahenthiralingam et al., "Nonmotility and phagocytic resistance of *Pseudomonas aeruginosa* isolates from chronically colonized patients with cystic fibrosis", Infect Immun., Feb. 1994, vol. 62, No. 2, pp. 596-605.

Dennis G. Maki et al., "Engineering out the Risk of Infection with Urinary Catheters", Emerging Infectious Diseases, vol. 7, No. 2, Mar.-Apr. 2001, pp. 1-6.

* cited by examiner

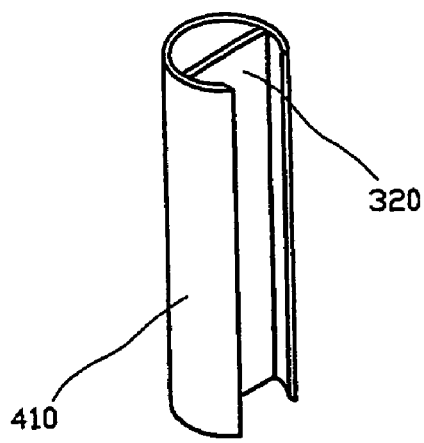
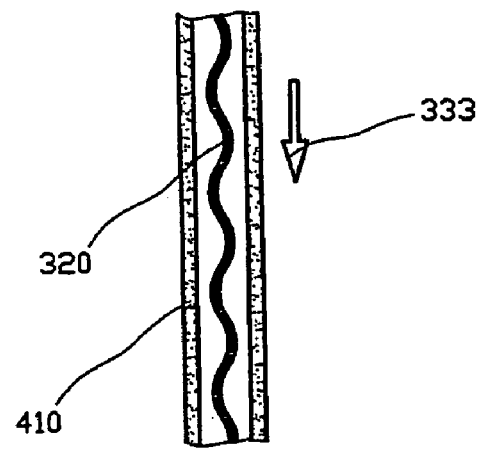
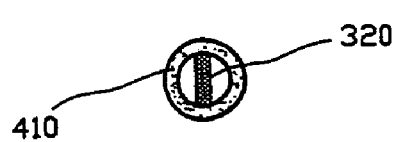
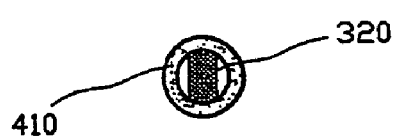
Fig. 8A
Fig. 8B
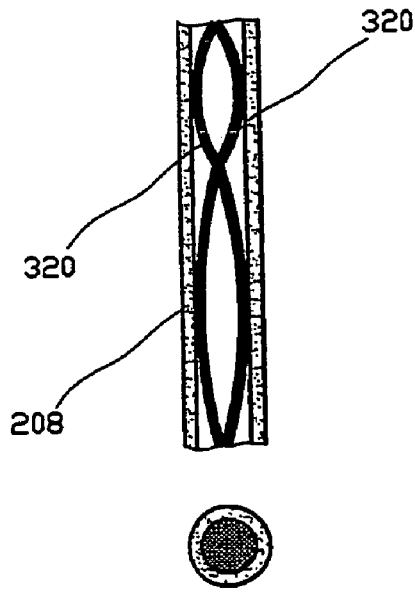
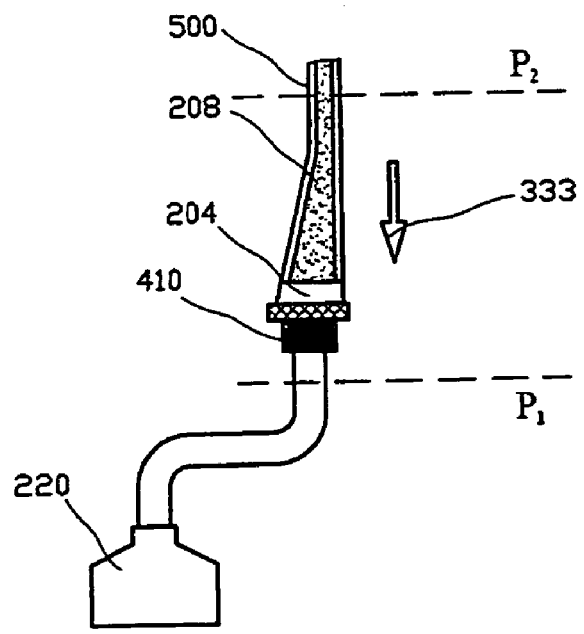
Fig. 8C
Fig. 8D
Fig. 8

Fig. 12 A
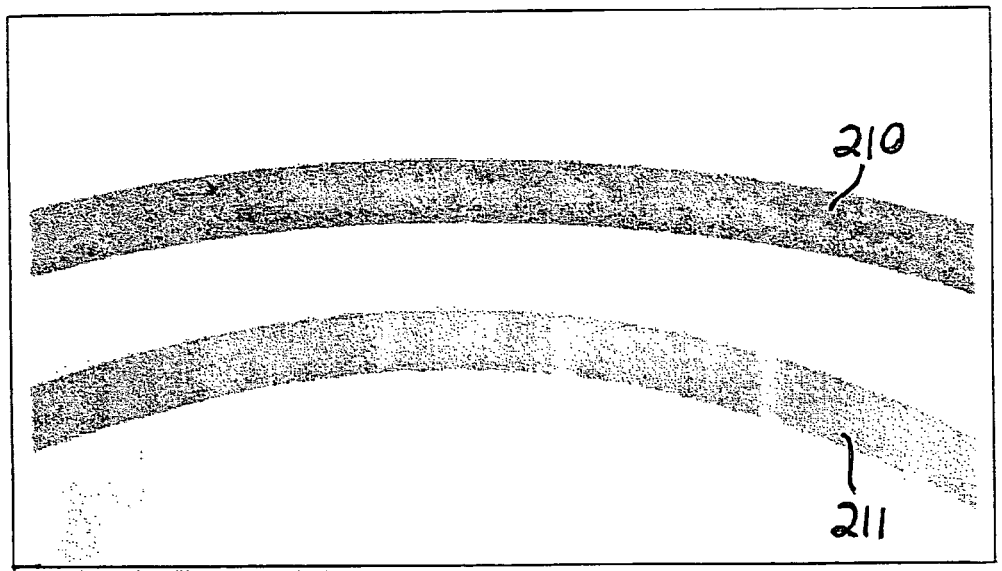
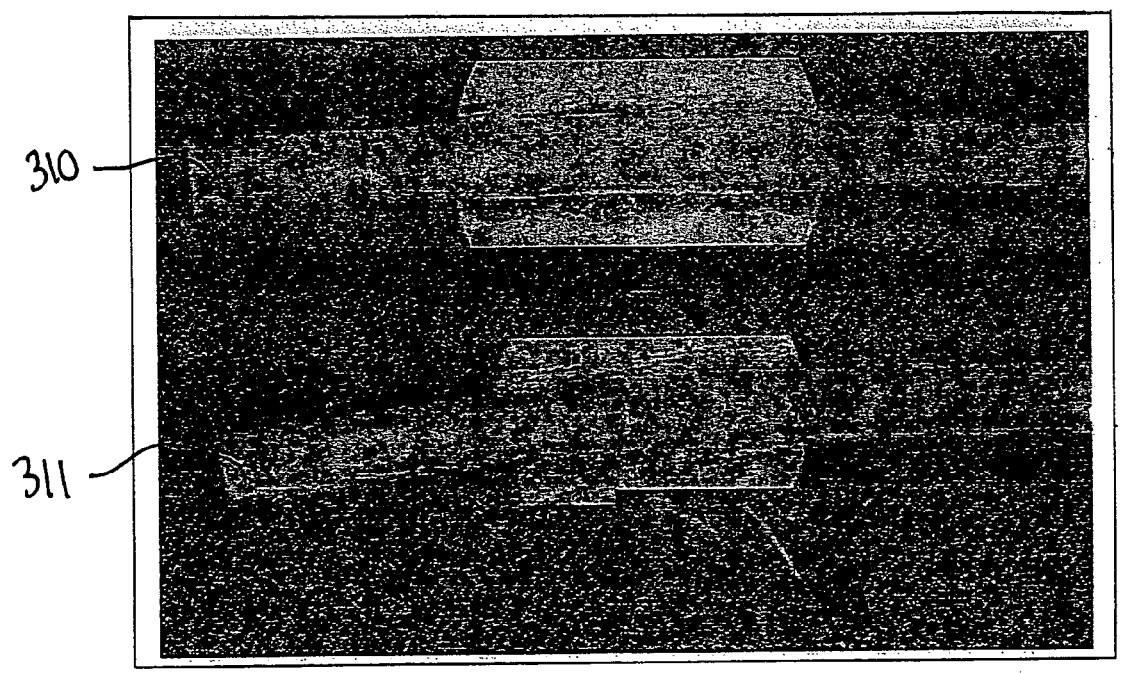
Fig. 12 B

METHOD, APPARATUS AND SYSTEM FOR TREATING BIOFILMS ASSOCIATED WITH CATHETERS

CROSS REFERENCE TO RELATED APPLICATIONS

This patent application claims the priority from U.S. Provisional Patent Application Ser. No. 60/383,592, filed on 29 May 2002, titled "METHOD AND SYSTEM FOR TREATING BIOFILM ASSOCIATED WITH CATHETERS", which is hereby incorporated by reference in its entirety.

FIELD OF THE INVENTION

The present invention relates generally to the field of acoustic medical devices, and more specifically to a method and system for using acoustic vibrations to treat biofilms associated with catheters.

BACKGROUND OF THE INVENTION

A catheter or tube may be inserted into an internal cavity or organ etc., through, for example, a body orifice or through a surgical procedure, and may be used for venting, feeding, and/or drainage of air and/or liquids to and/or from the internal cavity or organ. Catheters are associated with a significant risk of infection and other related medical problems. For example, infections are often associated with the development of pathogenic microorganisms, or biofilms, on the catheter surface and/or on the wall of the internal organ or cavity.

A biofilm may be formed when microbe adhere to surfaces in aqueous environments and begin to excrete a slimy, glue-like substance that can anchor them to material such as metals, plastics, soil particles, medical implant materials, and tissue. A biofilm can be formed by a single microbe species, but more often biofilm may consist of many species of microbe, as well as fungi, algae, protozoa, debris and corrosion products. Essentially, biofilm may form on any surface exposed to microbe and some amount of water. Once anchored to a surface, biofilm microorganisms carry out a variety of detrimental or beneficial reactions (by human standards), depending on the surrounding environmental conditions. Conventional methods of killing microbe (such as antibiotics and disinfectants) are often ineffective with biofilm microbe. Furthermore, huge doses of anti-microbials are generally required to rid systems of biofilm microbe.

Known methods for treating and/or preventing catheter-associated infections include the insertion of catheters using aseptic techniques, the maintenance of the catheter using closed drainage, the use of special non-standard catheters, and the use of anti-infective agents. The use of anti-infective agents may include soaking the catheter prior to insertion in an anti-infective drug solution, binding anti-infective agents to the catheter surface, continuous irrigation of the catheter balloon with an anti infective solution, and the insertion of anti infective drugs into catheter collection bags.

However, the prior art methods may not be sufficiently concentrated in the correct areas for microbial inoculation of catheters, especially for long-term treatment. Furthermore, antibiotic toxicity may develop due to the use of antibiotic anti-infective drugs. Additionally, the cost of utilizing catheters that are equipped with anti-infective drugs or which are not standard catheters is high. Finally, the infusion of such drugs into a patient's body must be considered and monitored for every case individually, in view of potential patient reactions to drugs, weakened immune systems, etc.

It would be highly advantageous to have a catheter system that can use standard catheters and yet more effectively and cheaply inhibit the formation of biofilms without the usage of anti-infective agents.

SUMMARY OF THE INVENTION

There is provided, in accordance with an embodiment of the present invention, an apparatus, system, and method for reducing pathogenic microorganisms (infections) resulting from the development of biofilms associated with catheters. According to some embodiments of the present invention, an acoustic apparatus, which may include at least one piezo-ceramic element and a vibration processor, may be integrated with standard catheters. This acoustic apparatus may use electric signals to generate vibrations to disperse microbe colonies, thereby preventing or dispersing biofilms that may cause infections. For example, mechanical signals such as micro-vibrations may be generated by the piezo-ceramic elements.

According to some embodiments of the present invention, the vibration processor may be adapted to provide resonance vibrations within the catheter or a stabilizing balloon, thereby significantly amplifying the vibrations relative to the amount of energy supplied.

Furthermore, according to some embodiments of the present invention, the piezo-ceramic element may be coated with a conducting material, and may have the shape of a ring, disc, valve, etc. The piezo-ceramic element may include a part for enabling the attachment of the element to the catheter. The vibration processor may include at least one megahertz oscillator and/or kilohertz oscillator, which may supply, separately or together, electric signals to and/or through the piezo-ceramic element(s).

The vibration processor may include a controller, switching gate, pulse supplier and analysis device. The analysis device may detect wave frequencies that may cause resonance in the catheter. The strength, duration, type, location, etc. of the waves may be controlled by the vibration processor and it's components.

According to some embodiments of the present invention, the vibration processor may provide electric signals to the piezo-ceramic element(s) such that the acoustic vibrations generated within the catheter may inhibit the entry of microorganisms from external sources.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein:

FIGS. 8A-8D are schematic illustrations of the operation of a piezo-ceramic element, according to some embodiments of the present invention;

FIGS. 12A and 12B illustrate results following experiments using vibrated and non-vibrated catheters.

DETAILED DESCRIPTION OF THE INVENTION

In the following description, various aspects of the present invention will be described. The following description is presented to enable one of ordinary skill in the art to make and use the present invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

The word "Microbe" as used hereinafter may encompass microorganisms, microbes, viruses, fungi, deposits, particles, pathogenic organisms, cells, and other bioactive materials. The word "pathogenic microorganisms" as used hereinafter may encompass any organisms, including bacterium or protozoan. Such organisms may be harmful, infectious, or non-harmful. The phrase "stabilizing balloon" as used hereinafter may encompass any type of catheter-based balloon. Stabilizing balloons may typically be used for stabilizing the position of a catheter within a canal, orifice, or organ etc. Other catheter balloons may be used.

In the description hereinbelow, the word catheter may refer to all types of catheters known in the art. The term catheter may include, for example, urinary, gastric, cardiovascular, and lung catheters, etc. Furthermore, the term catheter may include catheters that are coated with chemo-prophylactic, biocide, antimicrobial and anti-infective drugs etc. The acoustic apparatus may be applied to catheters used for medical, veterinary, or other purposes. Although catheters described herein generally refer to catheters with stabilizing balloons (balloons that may be expanded to secure the place of the catheter in the body cavity or organ etc.), catheters may also refer to catheters with no stabilizing balloons.

Figure 1B:
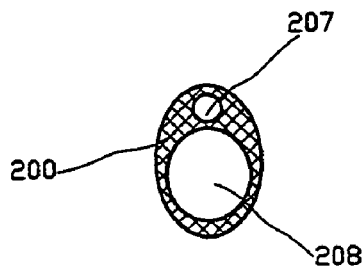
FIGS. 1A and 1B are schematic illustrations of a typical catheter and a cross section of a typical catheter respectively, which may be used with an embodiment of the present invention.
Figure 1A:
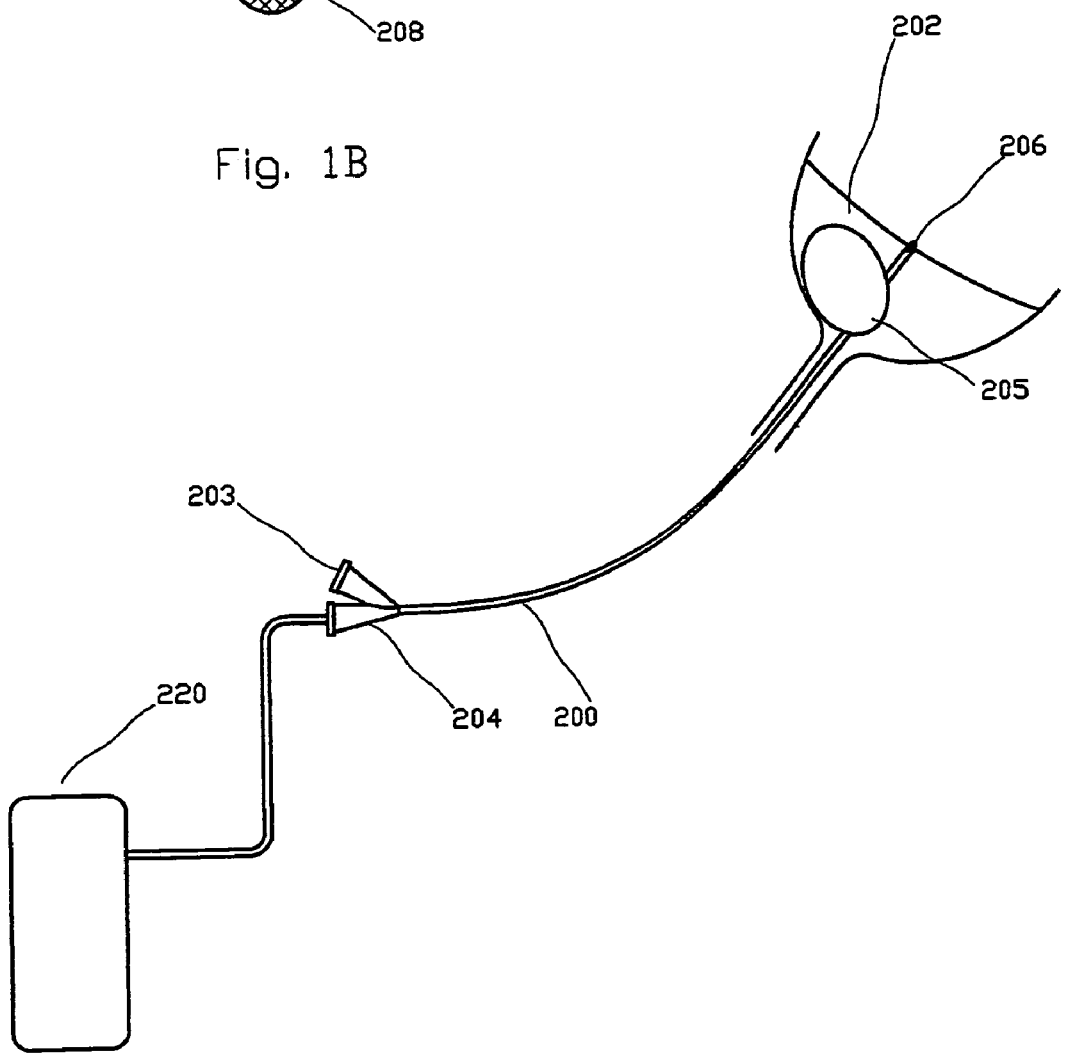

Reference is now made to FIGS. 1A and 1B, which are schematic illustrations of a typical catheter and a cross section of a typical catheter respectively. In the case of urinary catheters, for example, a urinary catheter 200, as can be seen in FIG. 1A, may be typically inserted through the urinary canal into the bladder 202. Catheter 200 may include a first and a second parallel inner tube along the catheter length. The parallel tubes are further illustrated in FIG. 1B, which is a cross section of catheter 200. First tube 207 may have a first valve 203 on one end and a balloon 205 on the other end. Second tube 208 may have a second valve 204 on one end and an opening 206 on the other end. A liquid and/or a gas may be transported through first valve 203 of first tube 207. The liquid/gas may inflate balloon 205 and thus may secure catheter 200 from sliding out of lumen 202, such as stomach, bladder etc. Fluid(s) and/or gas(es) from lumen 202 may enter opening 206 and flow through second tube 208 and through valve 204 into a bag 220 where they are collected. Alternatively, catheter 200 may be used to provide nutrition through second tube 208 into lumen 202. The above-described valves may include any of various devices that may regulate the flow of gases, liquids, or loose materials through catheter 200, by opening, closing, or obstructing ports or passageways etc.

Inner wall infections, such as bladder wall infections, for example, may be caused by catheter 200, possibly due to the formation of microbe colonies on or around catheter 200. Such infections may be divided to extra-luminal infections starting at the outer surfaces of catheter 200 and intra-luminal infections starting at the inner surfaces of catheter 200. Extra-luminal infections are infections initiated at the external surface of the catheter and may spread, for example, to the external surface of the bladder wall, to balloon 205 or to the bladder 202, for example. Intra-luminal infections are infections initiated at the inner area of the catheter, for example, in collection bag 220 or in second valve 204. These infections may spread, for example, to the upper part of the catheter 200 or to the bladder 202, for example, through opening 206. Extra-luminal and intra-luminal infections may further spread within a body, for example, to the kidneys, bladder, stomach, liver, colon, and the blood.

Figure 2:
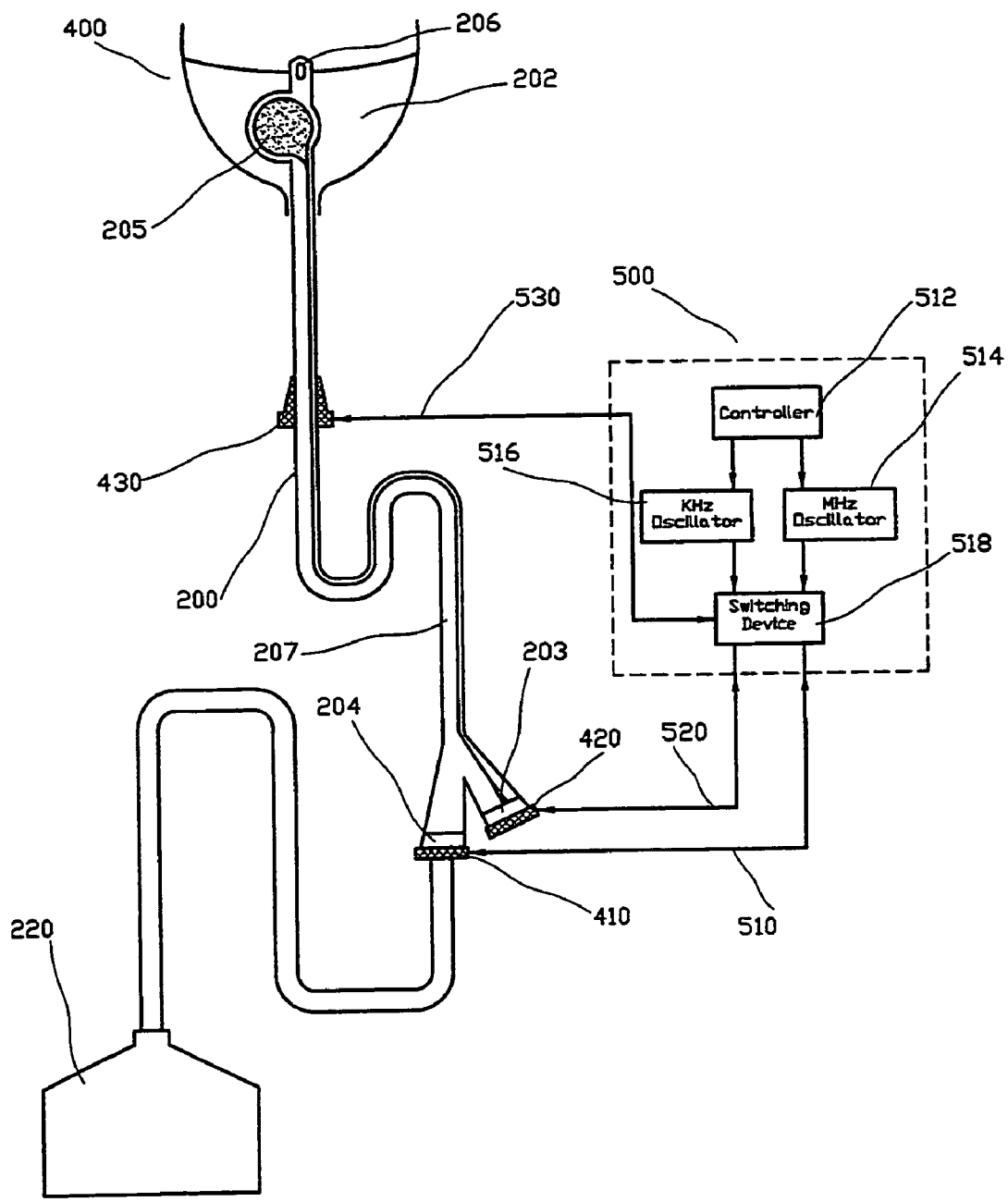
FIG. 2 is a schematic illustration of an acoustic apparatus for preventing biofilm formation and/or dispersing biofilm formations using the catheter of FIGS. 1A and 1B, according to some embodiments of the present invention.

Reference is now made to FIG. 2, which is a schematic illustration of an acoustic apparatus 400 functionally integrated with a catheter 200, according to some embodiments of the present invention. According to an embodiment of the present invention, an acoustic apparatus 400 is provided, which may prevent or treat the formation of microbe colonies. These microbe colonies may lead to the development of harmful biofilm(s), which may include various pathogenic microorganisms or infections. The acoustic apparatus may comprise at least one piezo-ceramic element and a vibration processing unit that, when attached to a standard catheter, may produce vibrations, for example micro-vibrations, which may disperse microbe colonies. The piezo-ceramic element may be attached to any conventional catheter such as, for example, a gastrostomy catheter, cardiovascular catheter, lung catheter, urinary catheter, etc. Any other catheters may be used. A processor, such as a vibration processor, may supply electric signals, which may be transformed by the piezo-ceramic element(s) to mechanical vibrations, such as sound waves. The vibrations may cause the piezo-ceramic element to oscillate thereby creating vibrations in the catheter and/or the relevant internal organs, cavities, passageways etc.

According to an embodiment of the present invention, the vibrations, which may be micro-vibrations, may be significantly amplified if a resonance condition is attained in the catheter, balloon and/or internal area. A resonance condition may cause an increase in the amplitude of oscillation of the acoustic apparatus when exposed to a periodic force whose frequency is equal to or very close to the natural undamped frequency of the apparatus. This resonance may intensify and/or prolong the acoustic vibrations generated by the piezo-ceramic element(s), relative to the energy supplied by the vibration processor. The effects of resonance may further aid in the dispersal of microbe colonies that have grouped around the catheter and/or the inner organs, or of the microbe colonies that are attempting to do so.

As can be seen with reference to FIG. 2, acoustic apparatus 400 may comprise at least one piezo-ceramic element, such as elements 410, 420 and/or 430 and a processor 500, hereinafter referred to as "vibration processor", which may be connected by electric wires 510, 520 and 530, for piezo-ceramic elements 410, 420, and 430 respectively. Any number of piezo-ceramic elements may be used.

Vibration processor 500 may include controller 512, megahertz oscillator 514, kilohertz oscillator 516, and switching device 518, which may include a summator, an amplifier, a receiver etc. Processor 500, together with a receiver may enable receipt of data from piezo elements 410, 420 and 430, and subsequent correction or optimization of usage of the piezo elements 410, 420, 430, by providing variable amplitudes and/or frequencies of micro-vibrations. Controller 512 may control megahertz oscillator 514 and kilohertz oscillator 516, which may be used to supply electric signals at megahertz (MHz) and kilohertz (KHz) frequencies, to piezo-ceramic elements 410, 420 and 430. Switching device 518 may control supplying MHz and/or KHz electric signals to piezo-ceramic elements 410, 420 and 430. Any combination of megahertz and/or kilohertz signals may be supplied to any combination of piezo-ceramic elements 410, 420 or 430. Thus, vibration processor 500 may supply electric signals at given frequencies to piezo-ceramic elements 410, 420 and/or 430 etc. To achieve micro-vibrations in piezo-ceramic elements 410, 420 and/or 430 piezo-electrical, piezo-magnetic, and any other suitable methods may be used.

Vibration processor 500 may generate electrical signals and transmit them to piezo-elements 410, 420 and/or 430. The electrical signals may hereby generate mechanical vibrations that may be transmitted through the catheter material, to balloon 205, lumen 202 and/or catheter end 206 etc., via channels 207 and 208. Each piezo-ceramic element 410, 420, 430 may oscillate separately, together or in any combination. The ceramic element may be tightly attached to an inner or outer catheter surface, and as a result of this attachment, vibrations from the ceramic elements may be transmitted through the catheter material, through inner catheter surfaces and/or through outer catheter surfaces, generating traveling mechanical waves. These mechanical micro vibrations may prevent biofilm formation on the catheter surface and/or disperse biofilm formations.

The types of vibration modes that may be created in the piezo-ceramic element may include, for example: thickness, longitudinal, torsion, flexural (bending)-flexural, longitudinal (radial)-flexural, radial-longitudinal, flexural (bending)-torsional, longitudinal-torsional and radial-shear modes etc., and any other suitable vibration modes. These vibration modes may be created separately or in any combination. Vibration modes may be enabled by varying the geometric shapes of the piezo-ceramic elements and/or the geometric shapes and placements of the relevant electrodes. Other suitable waves or vibration modes may be used.

Micro-vibrations from piezo-ceramics may be transmitted through catheter material and/or through inner/outer catheter surfaces. The vibrations transmitted through catheter material may have vibration modes that include, for example, thickness, longitudinal, torsion and flexural modes. These modes may be achieved separately or in any combination, as described below. The modes of vibrations achieved may be enabled by choosing particular piezo element geometries and placements. Vibrations transmitted through the catheter material may cause a weak surface vibration on the material. By combining vibration modes from piezo-ceramic elements it may become possible to intensify the surface vibrations, for example, by generating Lamb and/or Rayleigh vibration waves.

Figure 4:
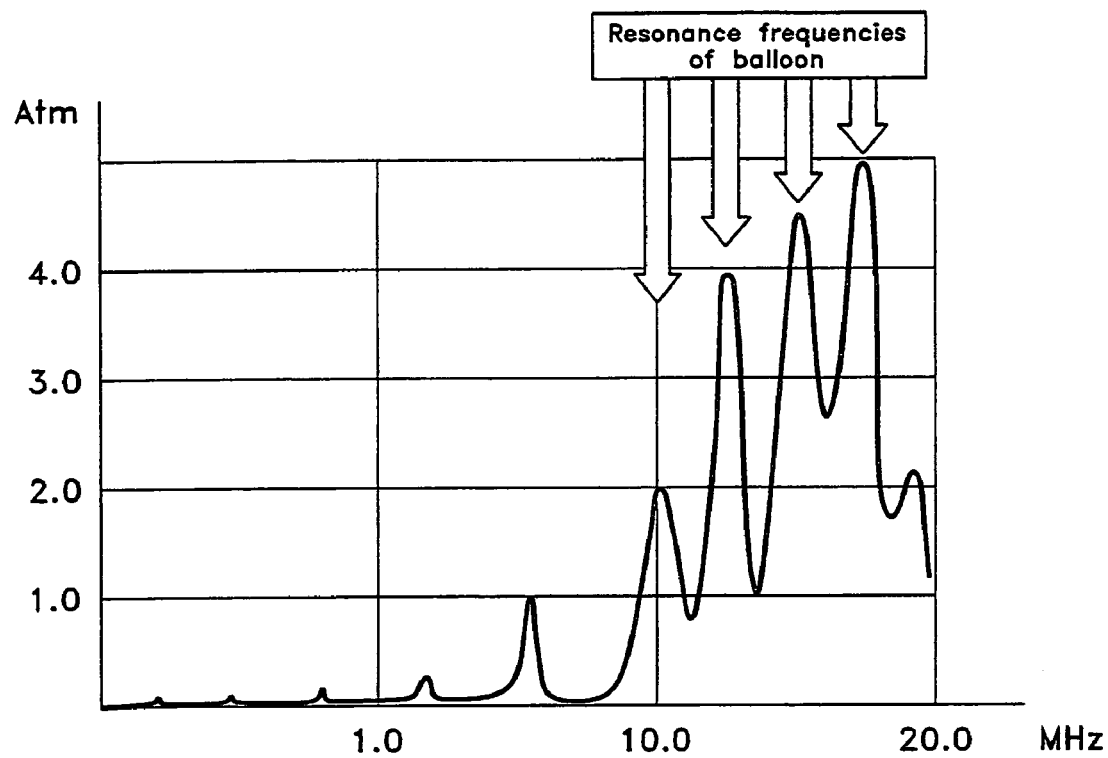
FIG. 4 is a graphical illustration of pressure in atmospheres as a function of frequency of supplied electrical signals, according to some embodiments of the present invention.

One end of the catheter may have a form of or include a balloon. The frequency and modes of vibrations in piezo elements (separately or in combination) may be chosen in such a way so as to achieve vibration resonance of the balloon volume (as it is shown in FIG. 4). As a result, the balloon itself may become a source of vibrations. These vibrations may be transmitted in different directions, for example, in the direction of the body, in the longitudinal direction of the catheter (through it's inner/outer surfaces), away from the body etc.

The frequency of transmitted waves may depend on the catheter type or construction (for example material, manufacturing etc.) and may not be the same as piezo-ceramic resonance frequency. By means of processor 500, in addition to choosing the proper resonance frequency of piezo ceramic elements, it may be possible to achieve effective vibrations on the surface of a catheter.

The vibrations from piezo elements and catheter surfaces may be transmitted to the liquids or materials that are in contact with the piezo elements. These liquids and materials may receive micro vibration energy, thereby preventing formation of biofilm.

The above mentioned combinations of vibration modes may be necessary since catheters in the market are made of different materials, manufactured in different resolutions, and every patient has different biofilms microbiology. To get the desired result, a particular combination of vibrations modes may need to be applied for each patient. Additionally, to generate resonance vibrations in the balloon, a particular combination of vibrations modes may need to be applied for each balloon. Since different balloons have different volumes and may be made of different materials etc., the outer loading of each balloon may differ. It may therefore be necessary to apply combinations of vibrations modes, to generate a mode that is similar to the natural vibration mode of the balloon, such that resonance of the balloon vibration may be achieved.

The vibrating of the balloon may act as an additional piezo element on the inner end of the catheter. The direction of the vibrations caused by the balloon may be different or opposite to the direction of the surface vibrations, caused by piezo elements. In this way biofilms may be transferred out of the body together with exiting liquids.

According to some embodiments of the present invention, vibration processor 500 may generate electrical signals that are applied to the electrodes of the piezo-ceramic elements, at a frequency that is typically in the MHz range. These electrical signals may excite piezo ceramic elements to vibrate in different modes or combinations of modes.

According to some embodiments of the present invention, vibration processor 500 may transmit electrical waves to an electrode of a piezo ceramic element, causing it to vibrate and to transmit these vibrations to catheter material in the form of through waves and weak surface waves. Intensifying surface vibrations, may generate, for example, Rayleigh waves and/or Lamb waves etc. It will be appreciated that other types of electrical signals may be applied alone or in combination with each other, as required, and any other waves or combination of waves may be implemented.

The amplitudes of excited vibrations on the catheter surface may be in the range of 10ths of nanometers. Any other suitable vibration ranges may also be utilized. Micro-vibrations may have a positive role of preventing trauma when applying and/or pulling out catheters. For these purposes vibrations in the range of 100 ds of nanometers may be applied. Any other suitable vibration ranges may be used.

In an embodiment of the present invention, piezo-ceramic elements 410, 420 and 430 may be coated with a suitable conducting layer such as, for example, silver, gold, nickel, conducting rubber or any other compatible conducting material.

Vibration processor 500 may be connected to piezo-ceramic elements 410, 420 and/or 430 via electric wires connecting the piezo-ceramic elements 410, 420 and/or 430 to vibration processor 500. These electrical connections may enable electric signals generated by vibration processor 500 to reach piezo-ceramic elements 410, 420 and/or 430, causing mechanical vibrations in piezo-ceramic elements 410, 420 and/or 430. Acoustic vibrations generated may include, for example, through waves and surface waves etc. Through waves may encompass, for example, one or more of: flexural (bending)-flexural waves, longitudinal (radial)-flexural waves, radial-longitudinal waves, flexural (bending)-torsional waves, longitudinal-torsional waves and radial-shear waves etc. Surface waves may encompass, for example, one or more of Rayleigh waves and/or Lamb waves. It will be appreciated that other types of electrical signals may be applied alone or in combination with each other, as required, to generate any type of vibration(s).

Figure 3:
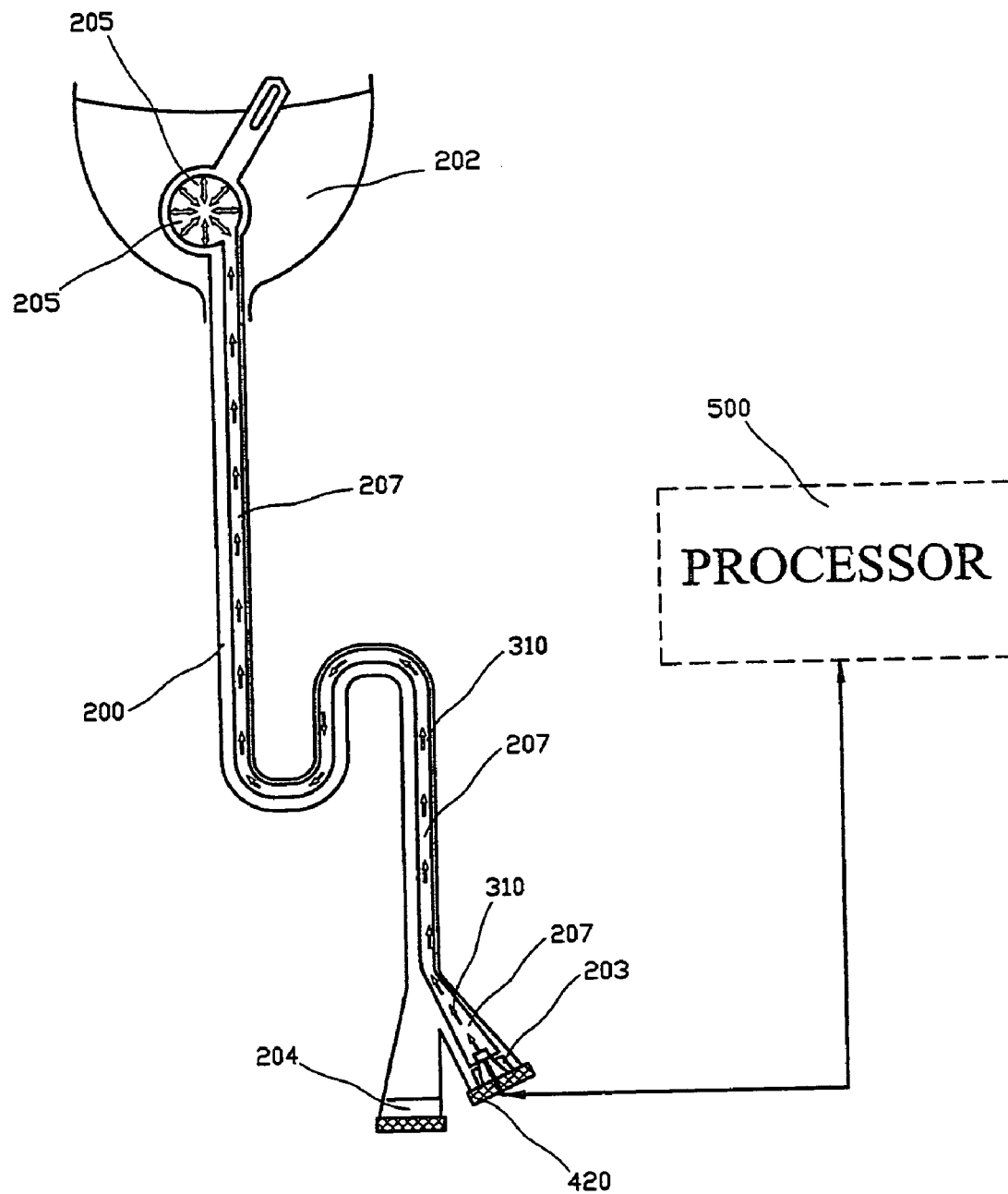
FIG. 3 is a schematic illustration of a processor connected to at least one piezo-ceramic element, where the piezo-ceramic is connected to the secondary (balloon inflation/deflation) tube of the catheter, according to some embodiments of the present invention.

Reference is now made to FIG. 3 illustrating the operation of piezo-ceramic element 420, attached to a secondary tube, such as 207, for inflating/deflating the catheter balloon 205 using gas or liquid. In response to the electric input generated by vibration processor 500, piezo-ceramic element 420 may oscillate, and vibrations (acoustic waves) as depicted by arrows 310 may be generated in liquid and/or gas entering channel 207, moving in the direction of balloon 205, lumen 202 and/or catheter end 206 etc. These vibrations may be in the megahertz range, thereby not being felt by a patient, yet having the power to substantially vibrate catheter 200 to prevent the formation of biofilm(s) and/or disperse biofilm in or around catheter 200, thus preventing or inhibiting the development of infections.

Piezo-ceramic elements 410, 420 and 430 may have any desired shape such as, for example, ring, disc, etc. The shape of the piezo-ceramic elements may influence the focus or direction of the vibrations generated in catheter 200. Accordingly, piezo-ceramic element 420 may be in a shape of a ring, disc or any other shape that may be applied to a conventional catheter or any other catheter. In an embodiment of the present invention piezo-ceramic element 420 may be in the shape of valve 203 and may thus replace catheter valve 203.

When applying electric signals generated by vibration processor 500 to piezo-ceramic element 420, piezo-ceramic element 420 may oscillate, and may further generate vibrations as depicted by arrows 310 in the liquid or gas filling first tube 207 and/or balloon 205. The vibration may be generated by applying MHz frequency electric signals, by applying KHz frequency electric signals or by applying a combination of MHz and KHz frequencies electric signals. The vibrations may prevent or inhibit the development of biofilm inside tube 207 and/or at the outer surface of catheter 200. Furthermore, vibrations may be initiated, for example, in balloon 205 and in lumen area 202, as a result of vibrations 310. These vibrations may prevent or inhibit the development of biofilm in balloon 205 and on the walls of the lumen 202. Furthermore, the acoustic vibrations may be generated according to a resonance frequency in balloon 205 and/or catheter 200, thereby generating resonance vibrations in catheter 200, balloon 205 and/or in lumen 202, thereby adding substantially to the impact of the vibrations. The resonance may be achieved when the natural balloon self-vibration and excitation vibrations are the same. The resonance of the balloon may depend on constant and/or variable parameters. In the case where a combination of vibrations is applied, one of the modes may correspond to the natural balloon self-vibration, causing it to vibrate in resonance.

Reference is now made to FIG. 4, which is a graphical illustration of the pressure in atmospheres as a function of the frequency of the supplied electric signals. The pressure developed within a spherical balloon 205 may be due to electric signals supplied through the piezo-ceramic element 420 by vibration processor 500. The graph shows that when applying signals at a frequency of up to approximately 8 MHz, a pressure that is less than 1 atmosphere may be developed in a spherical balloon. This frequency range may typically not be the resonance frequency of the spherical balloon. The graph also shows that when applying signals at a frequency of around 10 -20 MHz a pressure of around 4 atmospheres may be generated in a spherical balloon. This frequency range may be in the resonance frequency of the spherical balloon.

By matching the supplied signal frequency to the spherical balloon resonance frequency, the pressure developed in the liquid in the spherical balloon may be considerably higher than when the frequency is not the resonance frequency. Thus, the vibration(s) created in the spherical balloon may be stronger and may prevent or inhibit the formation of biofilm(s) more efficiently than when supplying electric signals that do not cause resonance in the spherical balloon.

It will be appreciated that balloon 205 may have shapes other than a sphere. For example balloon 205 may be oval, egg shaped, etc., according to the canal, vessel, passageway or body cavity being treated. The shape of balloon 205 may be one of the parameters determining the frequency required for achieving resonance in balloon 205 and may determine the location on which the vibration(s) focus in balloon 205, as will be described herein below.

According to some embodiments of the present invention, the signal frequency required for achieving resonance in balloon 205 may be found, for example, by transmitting acoustic vibrations to balloon 205 and monitoring the intensity of the vibrations received back. When the intensity of the received wave is the highest, balloon 205 is typically in resonance. Thus, the signal frequency that may enable the piezo-ceramic element(s) to transmit vibration(s) of high intensity may also be the signal frequency required for resonance.

Figure 5:
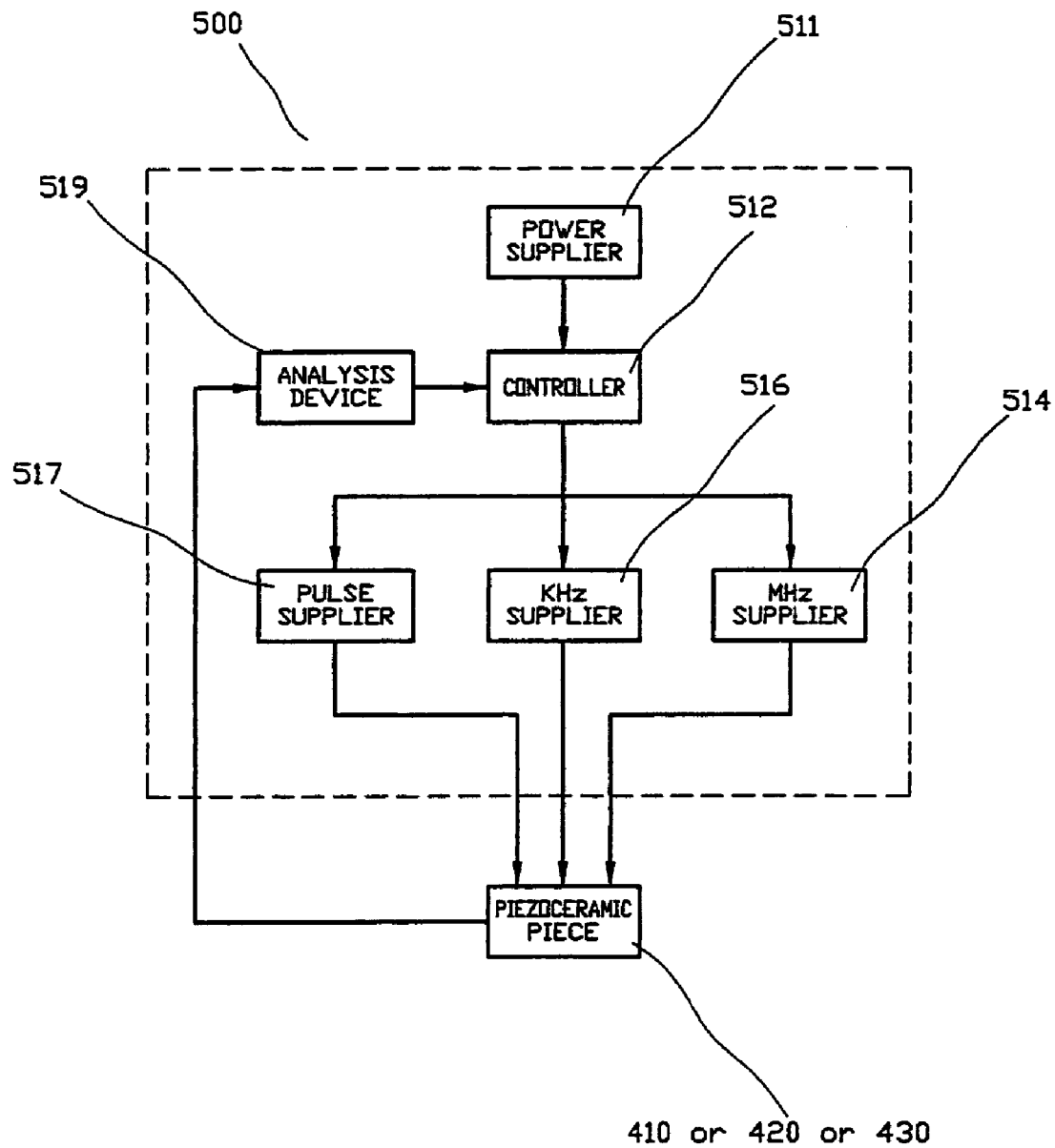
FIG. 5 is a more detailed block diagram illustration of the processor of FIG. 2 according to some embodiments of the present invention.

Reference is now made to FIG. 5, which illustrates components of vibration processor 500 operatively connected to one or more piezo-ceramic elements (410, 420, and/or 430) according to some embodiments of the present invention. Vibration processor 500 may include a power supply 511 (internal or external), a controller 512, MHz oscillator 516, KHz oscillator 514, a pulse supplier 517, and an analysis device 519. Controller 512 may control the various components of vibration processor 500, thereby managing, for example, the generation, transfer, receipt and/or processing of signals and vibrations. Controller 512 may control pulse supplier 517, which may transmit electric signals, such as electric pulses, having a known frequency. Vibration(s) may hit the inside wall of balloon 205 (FIGS. 2 and 3), and be reflected and received by analysis device 519. Analysis device 519 may send pulses, the resulting frequencies pulses, analyze pulses and vibrations etc., to enable provision of resonance frequencies. Analysis device may include switching device (518 of FIG. 2). Controller 512 may receive this input from analysis device 519 and may control MHz oscillator 514 and KHz oscillator 516 to supply the required electric frequency for obtaining frequency resonance in balloon 205. The above components may be placed in an outside box, or the in a "chip" that may be attached to a piezo element, or may be embodied in any other suitable combination of components. It will be appreciated that controller 512 may operate and/or interact with one or more of the piezo-ceramic elements, alone or in any combination.

Figure 6A:
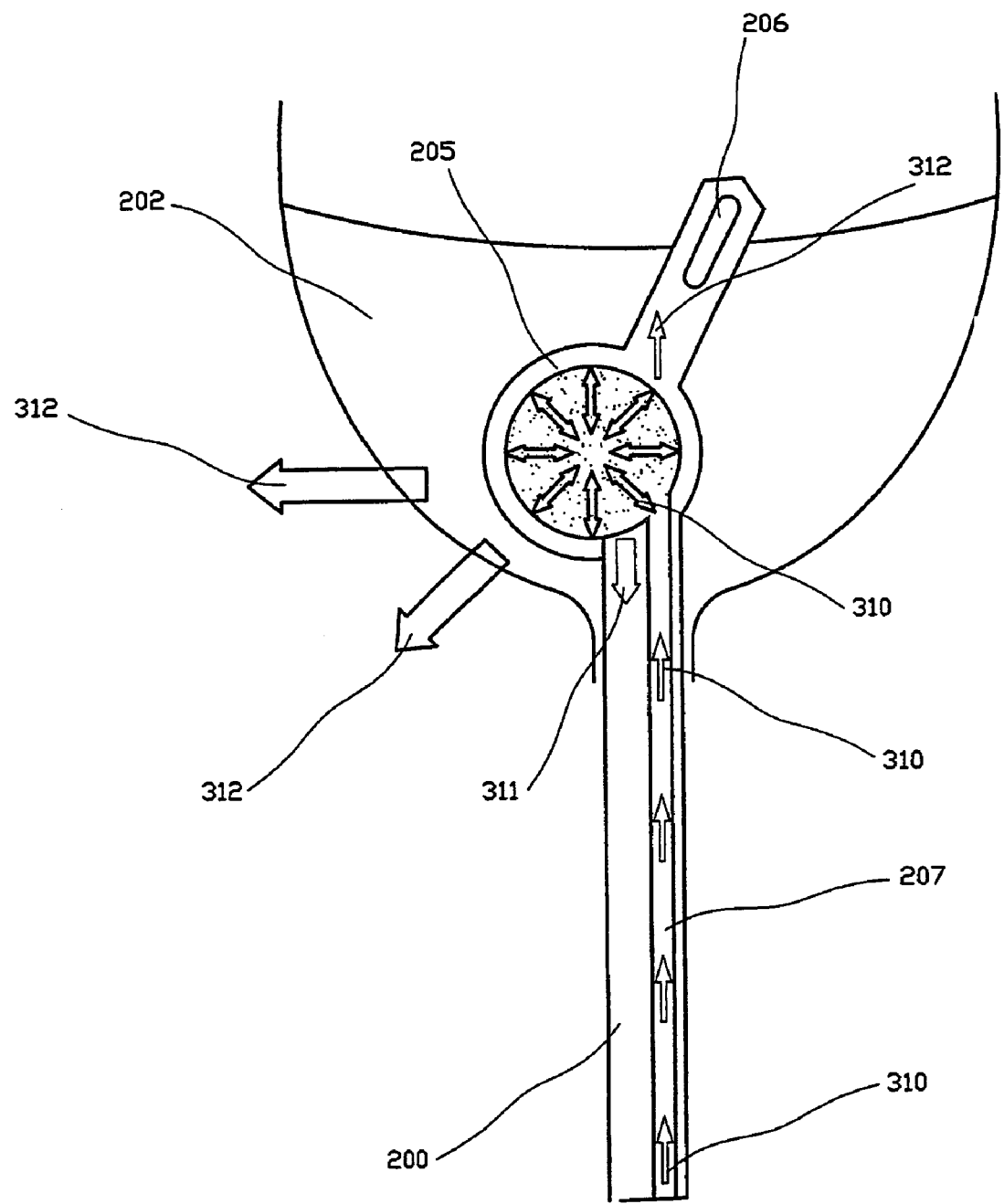
FIGS. 6A-6C illustrate the focus of vibrations in various balloon shapes, according to some embodiments of the present invention.
Figure 6B:
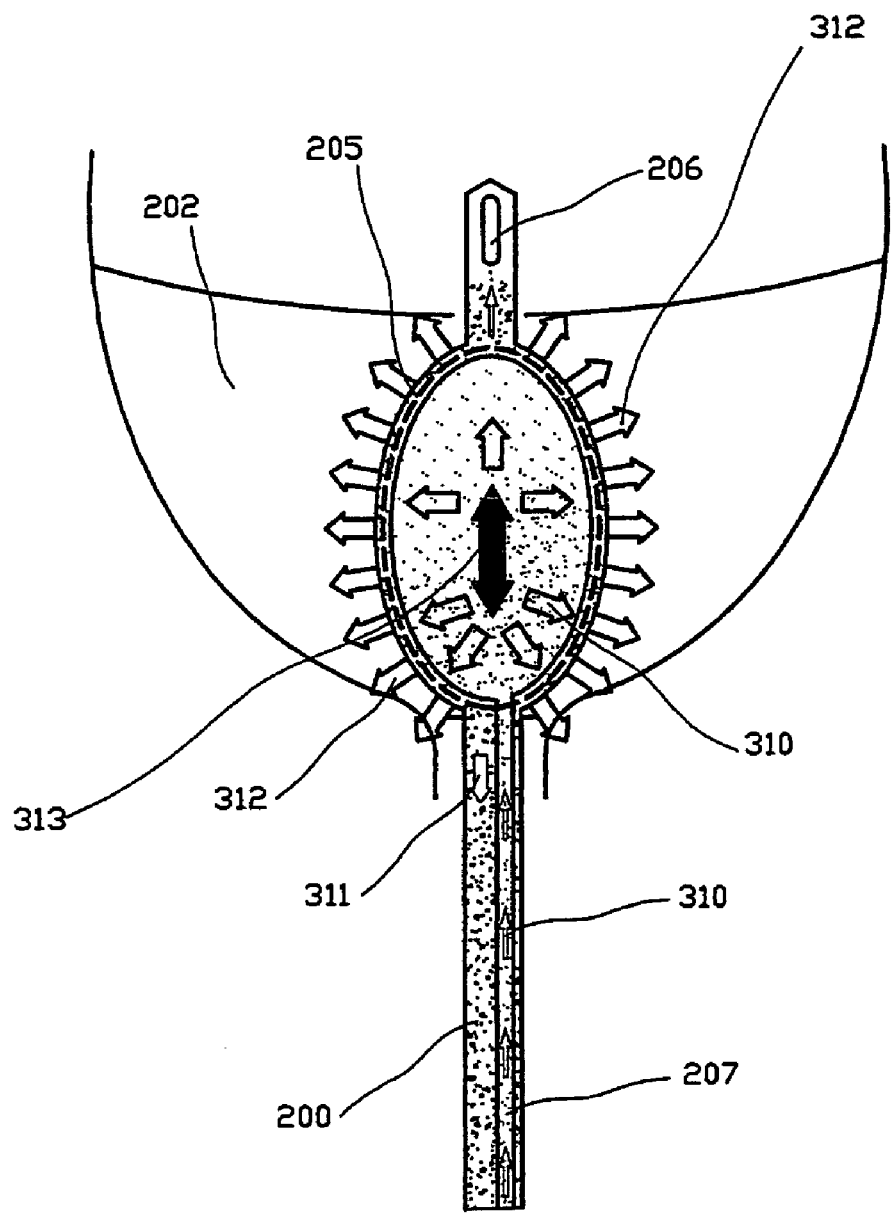
Figure 6C:
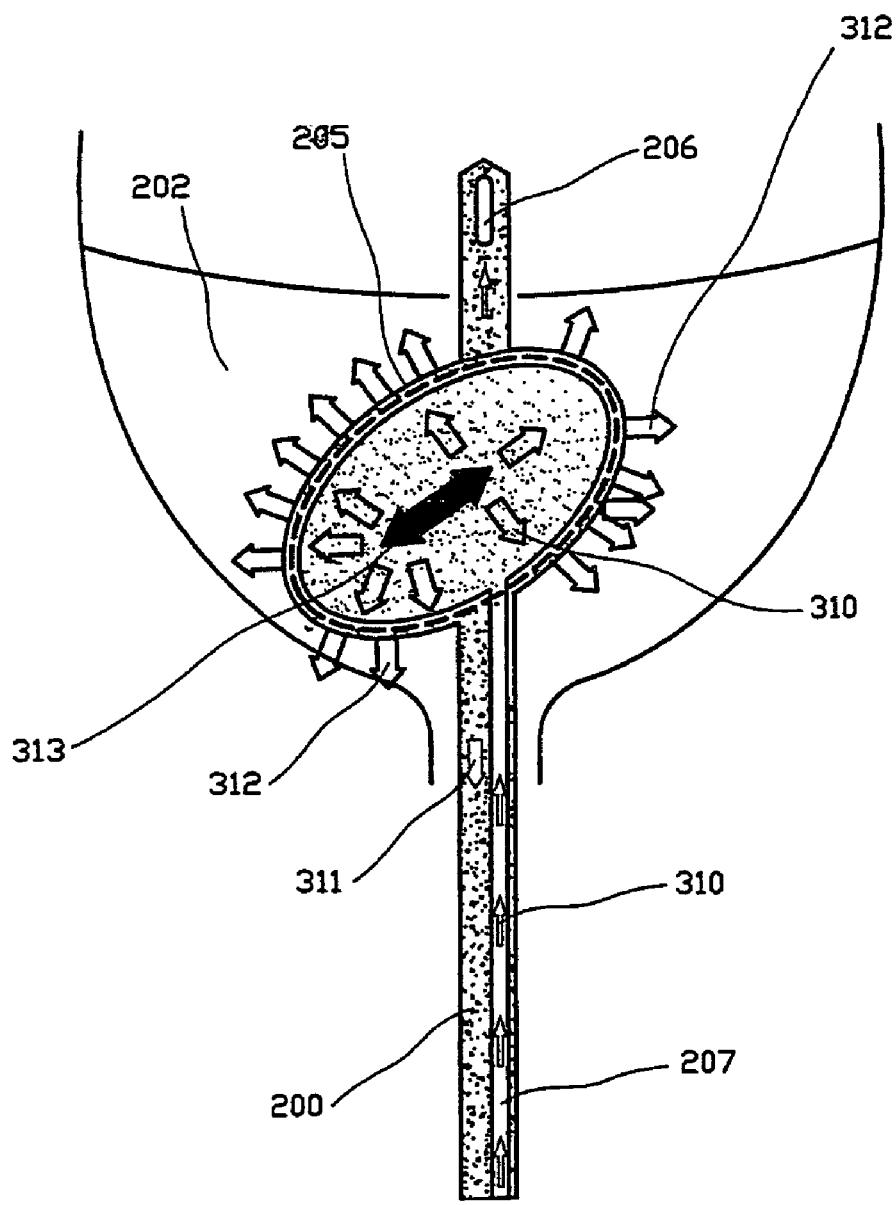

Reference is now made to FIGS. 6A-6C illustrating examples of some locations on which vibrations in various balloon shapes may be focused. The shape of balloon 205 may be determined by manufacture, and/or may be changed by controlling the flow of liquid and/or air to balloon 205. The focus or direction of the acoustic vibrations generated by balloon 205 may depend on, for example, the shape of balloon 205. As illustrated in FIG. 6A, when balloon 205 is in a shape of a sphere, the vibrations depicted by arrow 310 may be transferred equally in all directions. When the shape of balloon 205 is asymmetric, the vibrations may not be transferred equally in all directions, as can be seen by arrows 310 in FIGS. 6A and 6B.

FIGS. 6B and 6C illustrate examples of asymmetric balloons, wherein the axis of symmetry is designated by arrow 313. As can be seen in FIGS. 6B and 6C, the vibrations may be transferred asymmetrically in such asymmetric balloons, as depicted by arrows 310. Upon generating resonance vibrations in balloon 205, balloon 205 may vibrate, thereby generating vibrations indicated by arrows 311 and 312. Arrows 311 may describe the direction of vibrations transmitted through exiting liquid and/or through inner and outer surfaces of a channel. Due to the direction of 311 (away from the body), biofilms and microbial contaminations etc. may be transferred out of the body. Various balloon vibrations may be implemented by transmitting various electric signals to one or more piezo-ceramic elements, according to some embodiments of the present invention.

By changing the shape of balloon 205 it may be possible to focus and to scan the focused energy of micro-vibrations. For example, in a catheter such as 200, a piezo element may provide not only vibrations 310 in the direction of balloon 205, but also regulate the shape of balloon 205. Piezo element such as 420 in FIG. 3 may be attached to channel 207, which may be filled with liquid or gas. When the size of a piezo ceramic element such as 420 is expanded or shrunk, for example, it may influence the pressure of liquids and/or gases in balloon 205, as the pressure in balloon 205 is related to the shape of balloon 205. FIGS. 6B and 6C also illustrate the relation between symmetric axis 313 of balloon 205 in respect to catheter 200.

Arrow 310 may describe acoustic waves that are transmitted from piezo ceramics through a channel that is appointed for blowing the balloon. For example, in a urinary catheter a channel may be appointed for filling the balloon with liquid. These vibrations may excite the balloon to vibrate and optionally to reach vibration resonance, thereby forming an additional vibration generator. Arrows 312 may reflect the directions of the vibrations generated due to resonance balloon vibrations.

Figure 7:
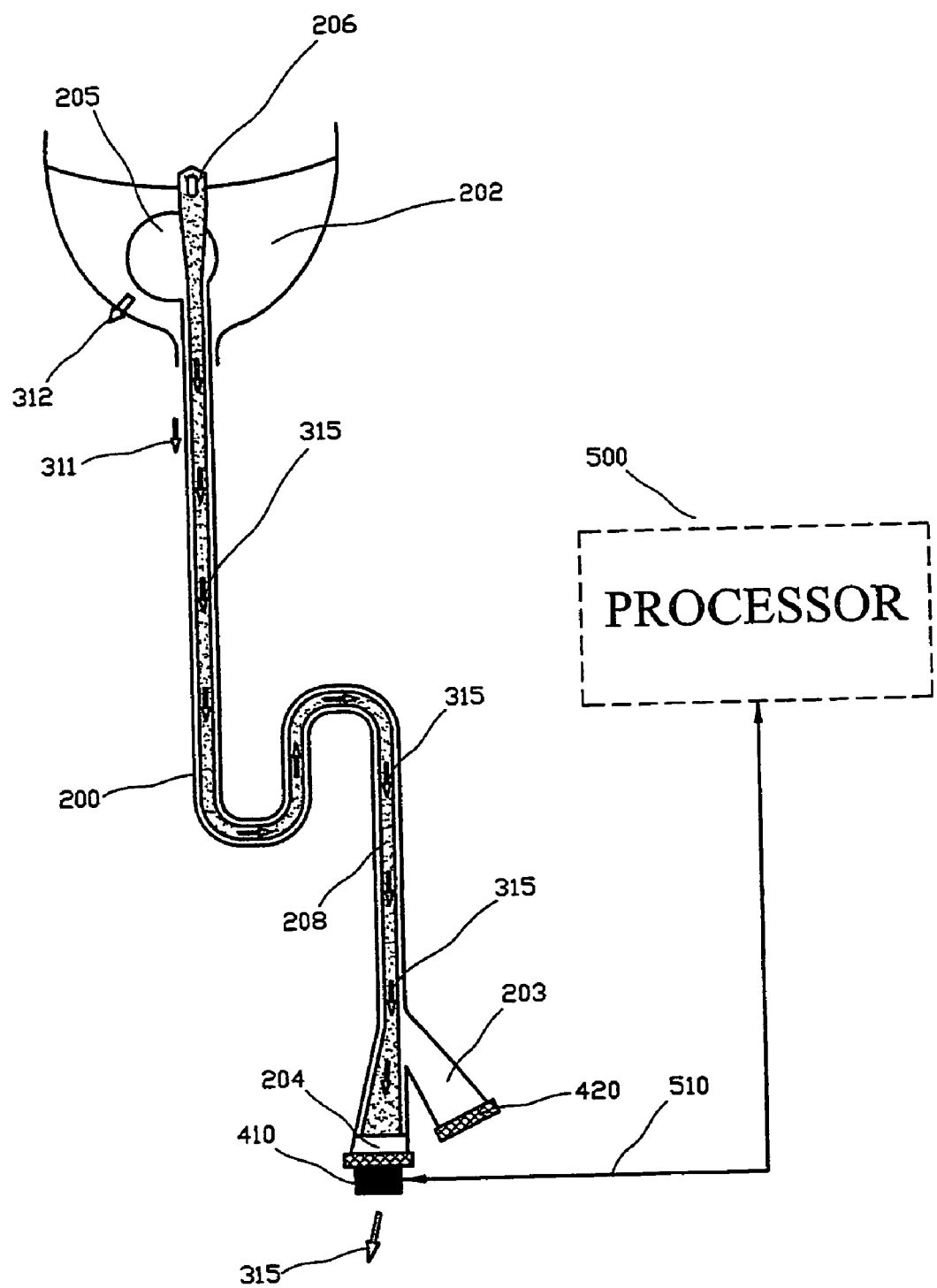
FIG. 7 is a schematic illustration of a processor connected to at least one piezo-ceramic element, where the piezo-ceramic connected to the main tube of the catheter, according to some embodiments of the present invention.

Reference is now made to FIG. 7 illustrating piezo-ceramic element 410 attached to a (main) tube 208 of catheter 200 and to vibration processor 500. Piezo-ceramic element 410 may be in a shape of a ring, disc or any other shape that may be applied to a conventional catheter or any other catheter. In an embodiment of the present invention piezo-ceramic element 420 may be in the shape of valve 203 and may thus replace catheter valve 203. Piezo-ceramic element 410 may be implemented in any other shapes. At least one conducting layer may coat Piezo-ceramic element 410.

Piezo ceramic element 410 may be placed adjacent to (or be integrated with) valve 204 of catheter 200. Catheter 200 may have an exit channel 208, which may play a critical role in the catheter's function. For example, in a urinary catheter this channel may serve to extract urine from the urinary tract. The direction of the uterine channel for extracting the urine may be designated by arrows 315.

When applying electric signals generated by vibration processor 500 to piezo-ceramic element 410, piezo-ceramic element 410 may oscillate thereby generating vibrations. The forms of these vibrations, as described above, may include: through (longitudinal, bending, thickness and their combinations) and surface (e.g., Lamb and Rayleigh) oscillations. These mechanical vibrations may be transmitted through inner and/or outer surfaces of channel 208, and through the liquid/gas in channel 207.

These vibrations may pass through catheter 200 to balloon 205, lumen 202 and/or catheter end 206 etc., and may, for example, generate resonance frequencies in balloon 205. Such resonance frequencies in balloon 205 may enable balloon 205 to generate vibrations, which may be dispersed in directions designated, for example, by arrows 312 and 311. In one embodiment, piezo element 410 may be attached to valve 204 of catheter 200 in such a manner that enables transmission of the vibrations through channel 208 in the direction of balloon 205, while no vibrations are transmitted through the outer surface of catheter 200.

In a case where vibrations are sent to balloon 205, lumen 202 and/or catheter end 206 etc., via channel 208, and after generating resonance frequencies in balloon 205 that create vibrations in the opposite direction, the oscillations that may occur in opposite directions, for example, in channel 207 to wards the catheter valve 420) may not be synchronized, and may cause unintended effects. The generation of pulses may therefore be controlled so as to avoid such unsynchronized vibration effects. For example, pulses generated by processor 500 may cease periodically, or during times that balloon 205 is generating or expecting to generate resonance vibrations. Furthermore, the piezo element 410 may transmit the vibrations away from the catheter, for example, towards collection bag 220, as indicated by arrows 315. Such vibrations may protect biofilm formation in, for example, the urinary bag 220.

The vibrating element 410 may be constructed in a shape that may enable the creation of vibrations similar to a pump action, for example, to extract exiting liquids. The vibrating element 410 may be in the shape of ring or cylinder and may excite standing waves in the ring/cylinder that may prevent (by "locking") microbe from getting into the catheter, for example, during the change of the collection bag. All the vibration forms described above may be used.

The vibrations may be generated by applying MHz frequency electric signals, by applying KHz frequency electric signals or by applying a combination of MHz and KHz frequency electric signals. The vibrations may prevent and/or inhibit the development of biofilm(s), for example, inside tube 208, at the outer surface of catheter 200, in lumen 202 and/or in the catheter bag 220.

One of the locations where infections may occur is valve 204. Infection may be initiated, for example, when valve 204 is opened to allow replacement of catheter bag 220, due for example, to the introduction of microorganisms from the outside environment. Piezo-ceramic element 410 may vibrate, according to some embodiments of the present invention, so as to prevent gas or liquid flow containing microorganisms through tube 208 while valve 204 is opened.

Reference is now made to FIGS. 8A-8D, which respectively illustrate various non-limiting examples of catheter valve configurations for blocking or limiting the flow of pathogenic microorganisms through a catheter, according to various embodiments of the present invention. The various configurations may be achieved, for example, by changing the wave frequency and the wave mode of acoustic vibrations generated by piezo-ceramic elements in the catheter. FIG. 8Ai illustrates a piezo actuator 410, having an internal valve or alternative piezo-ceramic element 320, made of piezo material, or partially made of piezo material. The vibrations of such a valve 320 may be such as to partially obstruct a channel, as can be seen in FIG. 8Aii.

FIG. 8Bi illustrates the case, according to some embodiments of the present invention, where pulses (electrical signals) from processor 500 generate running vibration waves (which may be longitudinal, bending, torsion or any combination of them) in the valve 320. In such a case, the direction of running waves is depicted by arrow 333, and the effect of such vibrating of valve 320 may be to obstruct a significant portion of a channel, as can be seen in FIG. 8Bii.

FIG. 8Ci illustrates the case, according to some embodiments of the present invention, where continuing electrical signals from processor 500 may generate standing vibration waves (which may be longitudinal, bending, torsion or any combination of them) in valve 320. The amplitudes of such standing waves may be the same as the inner diameter of piezo element 410, thereby blocking the entire channel, as can be seen in FIG. 8Cii. Such waves may serve as a "lock" to protect the catheter from the entry of microbe, for example, while changing the collection bag 220. Additional functionality may be achieved by applying short-term stress, such as periodic pulses at selected times and of selected strengths, to the catheter, to "shake off" microbe (biofilm) from the catheter surface (for example n times/day). Biofilm may be extracted by means of other vibrations, as described above.

FIG. 8D illustrates a biofilm treatment system, according to some embodiments of the present invention, attached to, for example, a urinary catheter 500. Running waves may be generated by the piezo element 410, causing different gas pressures in the catheter. For example, when the pressure at P2 is greater than the pressure at P1, the biofilm treatment system may work as a pump, thereby preventing the entry of microbe from the collecting bag 220 to the catheter 500.

Figure 9:
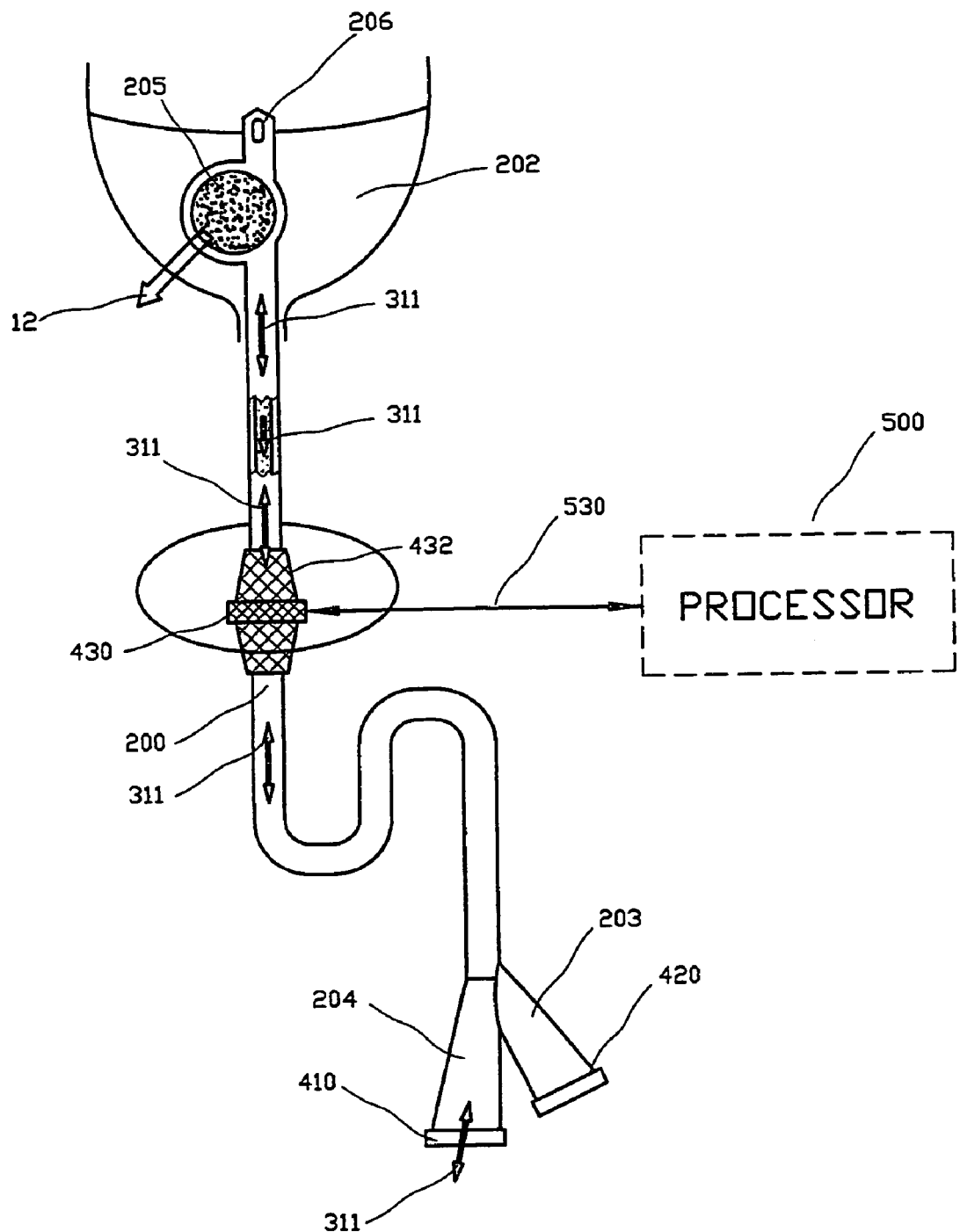
FIG. 9 is a schematic illustration of an acoustic apparatus attached to the body of a catheter, according to some embodiments of the present invention.

Reference is now made to FIG. 9 illustrating the operation of piezo-ceramic element 430 attached to a point on the outer surface of the body of the catheter 200 and operatively connected to a vibration processor 500, operative in accordance with an embodiment of the present invention. Piezo-ceramic element 430 may be in a shape of ring, disc or any other suitable shape that may be applied to a conventional catheter or any other catheter. Piezo-ceramic element 430 may comprise an additional part such as a ring 432 that may enable the adjustment of the attachment of piezo-ceramic element 430 to catheter 200, and allow transmission of vibrations from piezo element 430 to the catheter surface. The additional part may be made of any suitable material such as rubber, plastic, silicon, etc. At least one conducting layer may coat Piezo-ceramic element 430.

When applying electric signals generated by vibration processor 500 to piezo-ceramic element 430, piezo-ceramic element 430 may oscillate, thus generating vibrations as depicted by arrows 311 in the air and/or liquid filling first tube 207, second tube 208 and/or in the catheter surface 200 (see FIG. 1B). The vibrations 311 may be generated by applying MHz frequency electric signals, by applying KHz frequency electric signals or by applying a combination of MHz and KHz frequency electric signals. The vibrations 311 may prevent and/or inhibit the development of biofilm(s) inside tubes 207 and 208 and at the outer surface of catheter 200. Furthermore, vibrations 311 may be generated in balloon 205 and in organ (such as bladder etc.) 202. Vibrations 311 may prevent and/or inhibit the development of biofilm in balloon 205, in the internal organ, and on the walls 202 of the internal organ or cavity etc.

According to some embodiments of the present invention, piezo-ceramic element 430 may generate vibrations in the direction of at least one of the catheter's external sources, as shown adjacent to piezo-ceramic elements 410 and 420. Piezo ceramic element 430 may cause micro-vibrations (through and surface, as described above), and may further generate running waves. These waves may partially or completely block channels 207 and/or 208, thereby achieving the functions described in FIG. 8B and/or FIG. 8C.

To achieve higher micro-vibration energy of balloon 205, it may be necessary to attach piezo element 430 to the catheter on the side of the channel 207. The distance chosen for placing element 430 (between ceramic element and catheter surface) may enable the application of the maximum acoustic waves to the center of channel 207. This may be achieved by properly choosing the acoustic layer material, geometrical shape and physical properties, and the length of vibration waves generated by piezo element 430. The length of mechanical vibration waves generated by piezo element 430 may be regulated by processor 500, thereby enabling the attachment of the same piezo element to catheters made from various materials and having different diameters.

Figure 10:
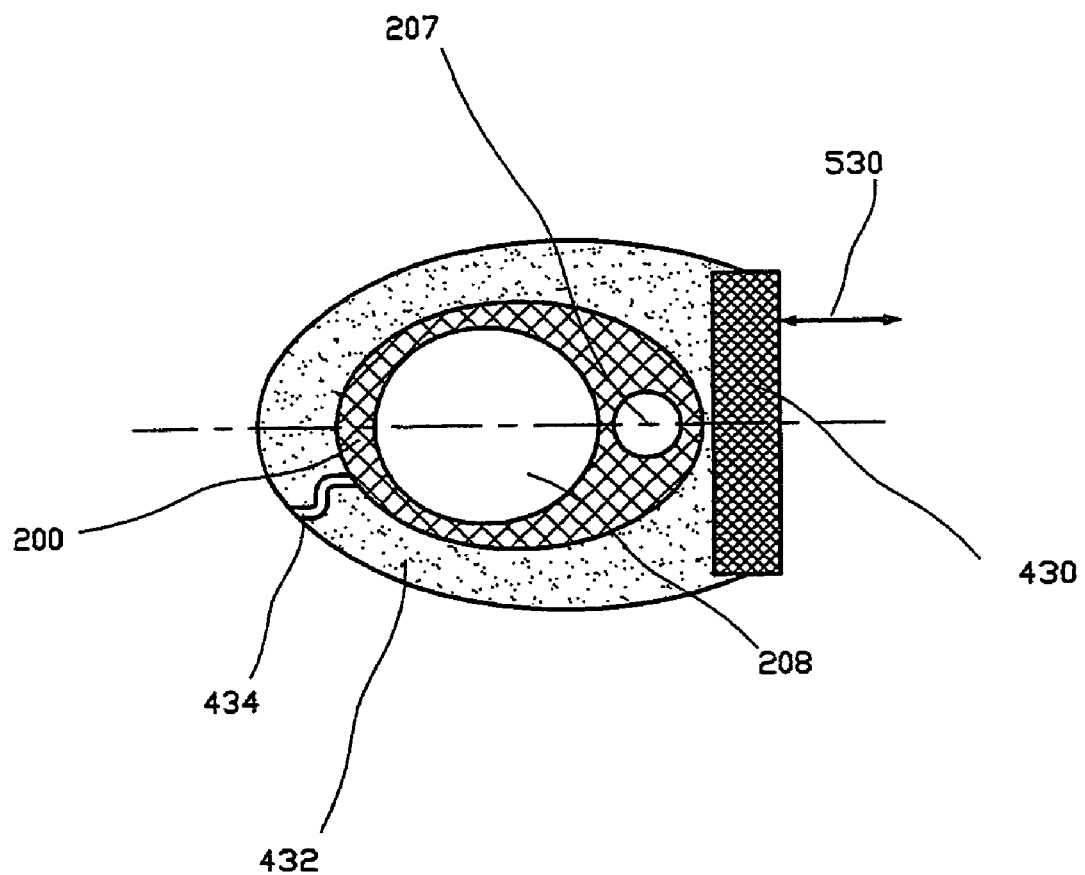
FIG. 10 illustrates a cross section of a catheter including a piezo-ceramic element, according to some embodiments of the present invention.

Reference is now made to FIG. 10 illustrating a cross section of catheter 200 including piezo-ceramic element 430, for example. Piezo-ceramic element 430 may be a square disc attached to ring 432, for example, or may have any other suitable shape. Ring 432, for example, may be made of electrically non-conducting material such as, rubber, silicone, plastic, etc. Ring 432 may have a cut 434, which may enable easy application of such a vibrating element to catheters of different diameters. Ring 432 may function to attach a piezo element to a catheter and to transmit mechanical vibrations from the piezo element to the catheter.

It will be appreciated that piezo-ceramic element 430 may operate alone or in combination with other piezo-ceramic elements. It will be further appreciated that piezo-ceramic element 430 may be constructed from various alternative materials, and may be formed in various shapes, according to the need.

It will be appreciated that additional piezo-ceramic elements may be applied on or integrated with catheter 200, for achieving various vibrations along the catheter and in the relevant canals, vessels, passageways, or body cavities. Furthermore, additional modes of vibration may be applied on piezo-ceramic elements 410, 420 and 430 etc., so as to achieve vibrations that may progress in various directions inside and outside catheter 200 and in the relevant canals, vessels, passageways, or body cavities.

Figure 11:
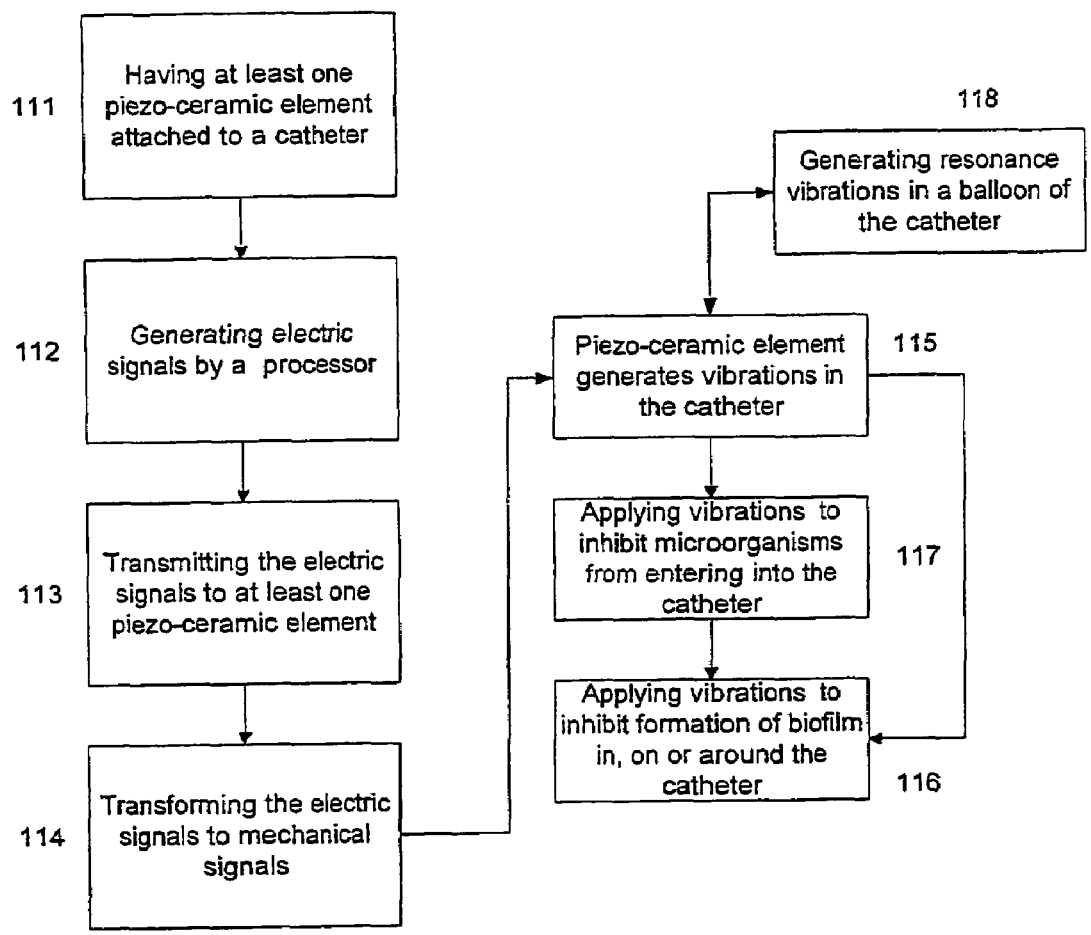
FIG. 11 provides a flow chart that describes methods of vibrating a catheter, according to some embodiments of the present invention.

According to some embodiments of the present invention, as can be seen with reference to FIG. 11, a method is provided for vibrating a catheter. Accordingly, at least one piezo-ceramic element may be attached 111 to a catheter. Electric signals may be generated 112 by a processor. Electric signals may be transmitted 113 to the piezo-ceramic element(s). The electric signals may be transformed 114 to mechanical waves in the piezo-ceramic element(s), and these waves may create 115 vibrations in the catheter. The vibrations may be applied 116 to at least one microbe colony to prevent formation of biofilm on, in or around the catheter. The vibrations may be applied 117 to the catheter to prevent microorganisms from entering the catheter from an external source. The processor may generate vibrations 118 that are matched to a resonance condition.

According to a further embodiment of the present invention, polyurethane tube catheters may be used, as may any other material. It is known by those skilled in the art that various materials have varying properties that impact, for example, on the extent to which acoustic vibrations are absorbed and/or dispersed by catheters. While the present invention has been described with respect to urinary catheters, the scope of the present invention may include any other suitable catheter types being used for various applications, including but not limited to the following:

| BODY SYSTEM | CATHETER TYPE | TYPICAL APPLICATION |
| --- | --- | --- |
| Cardiac | Angioplasty Balloon | Dilating coronary artery Stenosis and placing stent |
| Cardiac | Valvuloplasty Balloon | Dilating valve ring |
| Cardiac | Counter Pulsation Balloon | Treatment in Cardiogenic Shock |
| Peripheral vascular | Fogarty | Clot removal |
| Peripheral Vascular | Angioplasty | Dilating Vessel and stent placement |
| Pulmonary Artery | Swan-Ganz | Obtaining cardiac wedge-pressure |
| Trachea | Endotracheal tube | Stabilize the tube in the trachea |
| Tracheo-bronchial Tree | Fogarty Type | Foreign Body Removal |
| GI Tract | Balloon Catheter | Stricture Dilation |
| GI Tract | Fogarty Type | Stone and Foreign Body extraction |
| GI TRACT-Nutrition | Gastrostomy | Hold Gastrostomy in Place |
| GI Tract | Achalasia Balloon | Dilate LES in Achalasia |
| GI Tract Nutrition | Intragastric Balloon | Obesity Control |
| GI Tract | PDT Balloon | Deliver PDT |
| Urology | Foley Catheter | Position Urinary Catheter |
| Urology | Balloon Catheter | Stricture Dilation |
| Urology | Fogarty type | Stone removal |

Effective applications of micro vibrations, according to some embodiments of the present invention, have shown positive results. Following are descriptions of several experiments recently performed using piezo-ceramic generated micro-vibrations in catheters. The experiments, the equipment used, and the results are not meant to be limiting; suitable variations and other experiments and procedures are within the scope of the present invention. In one experiment, Dr Zadik Hazan of PMG Medica Laboratory (PMG Medica Ltd., Nesher, Israel) provided a minimal growth media containing water enriched with heterophylic microbe; control tube (1) and vibrated tube (2). The two tubes were placed in the solution for 14 days. The results showed that vibrated tube (2), using micro vibrations in amplitudes of nanometers, maintained its original color and transparency, while control tube (1) became heavily covered with mixed microbial biofilm. A photograph illustrating the results of this experiment can be seen with reference to FIG. 12A, illustrating the effects on control tube 210, and vibrated tube 211.

In a second experiment, Dr Zadik Hazan of PMG Medica Laboratory (PMG Medica Ltd., Nesher, Israel) provided a control latex tube diameter 16 mm) immersed in minimal growth media containing heterophylic microbe for 100 days. A similar latex tube was placed for 100 days in a similar medium, but was made to vibrate using micro vibrations in amplitudes of nanometers. The results showed that there were no signs of biofilm on the vibrating tube. Results also showed that the control tube was covered with a heavy layer of biofilm, as well as with scales. A photograph illustrating the results of this experiment can be seen with reference to FIG. 12B, illustrating the effects on control tube 310, and vibrated tube 311.

In a third experiment, undertaken between 12-19 Mar., 2003, by Dr Zadik Hazan of PMG Medica Laboratory (PMG Medica Ltd., Nesher, Israel) and Dr Gad Lavy (of Sheba Medical Center, Israel), 4 white rabbits weighing 4.5 kg each were used. The experiment aimed to evaluate the safety and preliminary efficacy of using microvibrated catheters to prevent microbial biofilm formation on catheters infected with *E. Coli* in New Zealand White rabbits. Accordingly, F8 urinary foley catheters (manufactured by UNO) were inserted into all 4 rabbits. The catheters were infected with uropathogenic *E. Coli* 106 per 1 ml, swabbed onto the portion of the catheter that was inserted into the meatus of each of the 4 rabbits. The infection was repeated three times on the first three consecutive days (suspensions provided by the Microbiology Laboratory of Sheba Medical Center, Tel Hashomer, Israel). The rabbits were housed in specially designed cages that prevented the animals from removing the catheters, while still allowing them some mobility. The rabbits were fed standard rabbit food and water ad. Libitum (unrestricted).

In two of the rabbits (1 and 2), the F8 catheters were connected to PZT elements made to vibrate, using micro vibrations in amplitudes of nanometers. Animals 3 and 4 received ordinary non-vibrated F8 latex Foley catheters. The animals were then observed for 8 days. On day 8 the animals were anesthetized, put down and the urinary tracts (urethra and bladder) removed and examined macroscopically. One animal (2) was excluded from the experiment because it removed the catheter 48 hrs prior to the termination of the experiment.

Figure 13:
FIGS. 13A, 13B and 13C illustrate results following experiments using vibrated and non-vibrated catheters in urinary tracts of animals.

A photograph illustrating the results of this experiment can be seen with reference to FIG. 13A, illustrating the effects on the urinary tracts of rabbits 1, 3 and 4. The left and center tracts are from control animals in which the catheters were not vibrated. The right bladder is from an animal in which the catheter was vibrated. As can be seen in the figure, the urinary bladder of animal #1 in which the catheter was vibrated was of a normal size of 4×2 cm (right panel of FIG. 13A). Animal #3, which had an un-vibrated ordinary urinary catheter F8, had a bladder size of 9×3.5 cm with a lighter texture and thinner, distended walls (left panel of FIG. 13A). Animal #4, which had an un-vibrated ordinary urinary catheter F8, had a grossly enlarged urinary bladder 11×4.4 cm in size with distended thin walls and a white texture indicating large amounts of pus (middle picture of FIG. 13A). After clearance of the piourea, the walls of the urinary bladder of animals 3 and 4 were found to be thin and floppy, the blood vessels gorged, inflamed and enlarged.

Figures 13, 13C:
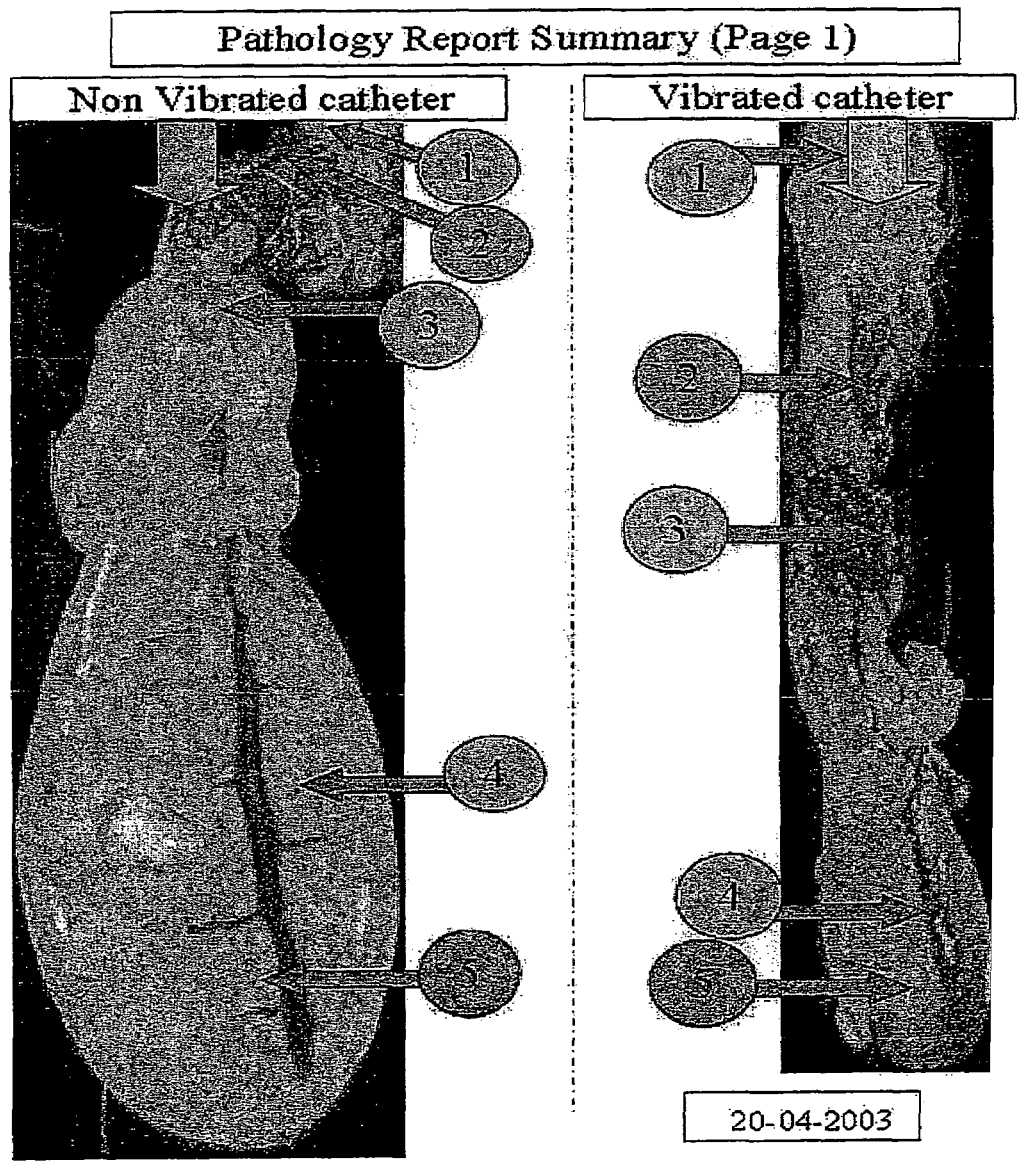

The third experiment (above) was followed up by a pathology report, based on a macroscopic examination performed by B. Czernobilsky, MD, Professor of Pathology at PATHOLAB. As can be seen with reference to FIGS. 13B and 13C, comparing animals 1 (vibrated Catheter) and 4 (non-vibrated catheter), comparative analyses were undertaken at stages 1, 2, 3, 4 and 5:

1—Distal Uretha: With animal 1, the entire mucosa is replaced by necrotic material, fibrin, and an inflammatory infiltrate composed predominantly of neutraphiles. The Lamina proprea is only focally involved. In the muscular wall there are a few foci of perivascular lymphocytes. With animal 2 the bladder in lined partly by normal appearing transitional cell epithelium. In other areas only a few layers of transitional cell epithelium are present, and in others there is no epithelium at all, or only one layer of basal cells. Lymphocytes with few neutraphiles, eosinophiles and occasional histiocytes are present in the Lamina propria. The Lamina propria shows some edema. The muscular wall, which is rich in blood vessels, shows no abnormalities.

2—Medial Uretha: With animal 1, the histological changes are similar to stage 1, however there are areas of intact mucosa on both sides of the necrotic process. This intact mucosa shows an acute inflammatory infiltrate, and at the edge of the slide, the necrotic process is again evident. With animal 2, the medial uretha is similar to the distal uretha.

3—Proximal Uretha: With animal 1, the mucosal layer is intact. Adjacent to the mucosa in the lamina propria there is a collection of neutrophiles and in its center Fibrin. Another such collection appears to be within a venous space. The muscular layer is not remarkable. On the serosal aspect there are few hemorrhagic areas. The thickness of the muscular layer in the urethal section is 0.8 to 1 mm. With animal 2 there are only few foci in which the transitional cell epithelium is present. In the rest, the lining cells are entirely absent, or show tiny strips of basal cells. The rest of the specimen is identical to the medial uretha. The thickness of the muscular layer in the urethal section is 0.5 to 1 mm.

4—Mid-Urinary Bladder: With animal 1, there are no abnormalities in the mucosa, lamina propria and muscular wall. With animal 2 the epithelial layer is lacking almost throughout. Only a few tiny foci show isolated epithelial cells. No inflammatory cells are present. In the bladder wall there is evidence of edema in the sub-epithelial layer. The muscular wall is intact.

5—Fundus of Bladder: With animal 1, no abnormalities are found. With animal 2, the histological picture is to that of the mid urinary bladder, except for the fact that the epithelial lining cells are entirely absent. The thickness of the muscular layer in the bladder sections is 0.5.

The preliminary description hereby presented suggests that the "Microvibrated Catheter" technology may be effective in in vivo animal models.

The foregoing description of the embodiments of the invention has been presented for the purposes of illustration and description. It is not intended to be exhaustive or to limit the invention to the precise form disclosed. It should be appreciated by persons skilled in the art that many modifications and variations are possible in light of the above teaching. It is intended that the scope of the invention be limited not by this detailed description, but rather by the claims appended hereto.

The invention claimed is:

1. A method for inhibiting biofilm formation associated with an indwelling catheter, the catheter comprising a stabilizing balloon, an inflation channel, and a vibrating piezo element coupled to a surface of the catheter, the method comprising:
  causing the piezo element to vibrate in a combination of vibrational modes, to cause a combination of acoustic wave modes, the combination of acoustic wave modes causing:
    surface acoustic waves to be generated on the external and internal surfaces of the catheter, wherein the wave type of the surface acoustic waves is selected from the group consisting of Rayleigh and Lamb waves;
    an acoustic wave to be generated in a liquid filling the inflation channel; and
    resonance in the stabilizing balloon, the resonance within the stabilizing balloon generating vibrations in liquid exiting the catheter and surface acoustic waves on the catheter;
  wherein the surface acoustic waves inhibit biofilm formation on surfaces of said catheter.

2. The method according to claim 1 wherein the vibrations in the piezo element are selected from one or more of the group consisting of: thickness, longitudinal, torsion, flexural (bending)-flexural, longitudinal (radial)-flexural, radial-longitudinal, flexural (bending)-torsional, longitudinal-torsional, and radial-shear.

3. The method according to claim 1, wherein the piezo element generates running or standing vibration waves in the catheter wherein the amplitudes of said waves are in the nanometer scale, wherein the frequencies of said waves are in the KHz-MHz scale.

4. The method according to claim 1, wherein the piezo element has a shape selected from the group consisting of a ring shape, disc shape, valve shape, and a combination thereof.

5. The method according to claim 1, wherein the piezo element is coated wit a layer, the layer selected from the group consisting of silver, gold, and nickel.

6. The method according to claim 1, comprising supplying electric signals to the piezo element, the signals being selected from the group consisting of: megahertz frequency signals and kilohertz frequency signals.

7. The method according to claim 1, wherein the piezo element applies periodic pulses to dislodge bacteria from the surface of the catheter.

8. The method according to claim 1, wherein the surface acoustic waves created by the balloon block microorganisms from entering the catheter.

9. The method according to claim 1, wherein the surface acoustic waves resulting from the piezo element and the surface waves resulting from the balloon are unsynchronized.

10. The method according to claim 1, the combination of acoustic wave modes causing vibrations acting as a pump to extract liquids from the catheter.

11. The method according to claim 1, the combination of acoustic wave modes causing vibrations which prevent microbes from entering the catheter.

12. The method according to claim 1, the combination of acoustic wave modes causing running waves causing gas pressure in the catheter.

13. The method according to claim 1, the combination of acoustic wave modes causing standing waves preventing microbes from entering the catheter.

14. The method according to claim 1, the combination of acoustic wave modes causing resonance vibrations in the catheter.

15. The method of claim 1, the combination of acoustic wave modes causing vibrations to prevent trauma when inserting or pulling out the catheter.

16. The method according to claim 1 wherein vibrations generated from the resonance created in the stabilizing balloon are transmitted on the surface of the catheter in an opposite direction to the vibrations transmitted on the surface of the catheter by the piezo element.

17. The method of claim 1, wherein vibrations generated by the piezo element travel towards a body in which the catheter is inserted and the surface acoustic waves generated by the balloon travel away from the body.

* * * * *